(12) United States Patent
Brown

(10) Patent No.: US 11,730,694 B1
(45) Date of Patent: Aug. 22, 2023

(54) HAIR COLORING COMPOSITIONS AND METHODS

(71) Applicant: L'OREAL, Paris (FR)

(72) Inventor: Jennifer Brown, Bloomfield, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/824,216

(22) Filed: May 25, 2022

(51) Int. Cl.
*A61Q 5/10* (2006.01)
*A61K 8/9789* (2017.01)
*A61K 8/894* (2006.01)
*A61Q 5/06* (2006.01)

(52) U.S. Cl.
CPC ............ *A61K 8/9789* (2017.08); *A61K 8/894* (2013.01); *A61Q 5/065* (2013.01); *A61K 2800/432* (2013.01); *A61K 2800/87* (2013.01)

(58) Field of Classification Search
CPC .................. A61K 8/9789; A61K 8/894; A61K 2800/432; A61K 2800/87; A61Q 5/065
USPC ........... 8/405, 407, 425, 455, 509, 540, 606, 8/637.1, 643
See application file for complete search history.

(56) References Cited

U.S. PATENT DOCUMENTS

| | | |
|---|---|---|
| 2002/0041854 A1 | 4/2002 | Hadasch et al. |
| 2003/0175328 A1 | 9/2003 | Shefer et al. |
| 2003/0175333 A1 | 9/2003 | Shefer et al. |
| 2004/0066299 A1 | 4/2004 | Hanabusa et al. |
| 2004/0132667 A1 | 7/2004 | Lintner |
| 2004/0164866 A1 | 8/2004 | Hanabusa et al. |
| 2005/0002996 A1 | 1/2005 | Sojka |
| 2005/0129759 A1 | 6/2005 | Sojka |
| 2005/0188480 A1* | 9/2005 | Lim ...................... A61K 8/411 8/405 |
| 2007/0074355 A1 | 4/2007 | Lee |
| 2007/0264204 A1 | 11/2007 | Noor et al. |
| 2007/0269399 A1 | 11/2007 | Tagawa |
| 2008/0166303 A1 | 7/2008 | Tamarkin et al. |
| 2008/0226684 A1 | 9/2008 | Peppas |
| 2008/0275118 A1 | 11/2008 | Shaw et al. |
| 2009/0093063 A1 | 4/2009 | Anslyn et al. |
| 2009/0117067 A1 | 5/2009 | Baltimore |
| 2009/0232857 A1 | 9/2009 | Peppas |
| 2011/0217249 A1 | 9/2011 | Dreher |
| 2012/0065115 A1 | 3/2012 | Johnson |

(Continued)

FOREIGN PATENT DOCUMENTS

| | | |
|---|---|---|
| CA | 3011390 A1 | 7/2017 |
| DE | 102008061861 A1 | 6/2010 |

(Continued)

OTHER PUBLICATIONS

English transaltion of the Patent No. WO 2010072577 A2. dated Sep. 22, 2022.*

(Continued)

*Primary Examiner* — Eisa B Elhilo
(74) *Attorney, Agent, or Firm* — Polsinelli PC

(57) ABSTRACT

The present disclosure relates to a hair coloring composition comprising aloe barbadensis leaf juice, direct dyes, polyether-modified polysiloxanes, and alkoxylated nonionic surfactants. The compositions are useful for coloring hair and can be applied directly to the hair, for example, as a spray formulation. The present disclosure also relates to methods for coloring hair and method for making the hair coloring compositions.

19 Claims, 2 Drawing Sheets

(56) References Cited

U.S. PATENT DOCUMENTS

| | | |
|---|---|---|
| 2012/0076742 A1 | 3/2012 | Phillips et al. |
| 2012/0192889 A1* | 8/2012 | Schmelz ............... A61K 8/046 |
| | | 8/408 |
| 2012/0230968 A1 | 9/2012 | Worden, Sr. |
| 2012/0263660 A1 | 10/2012 | Altschul et al. |
| 2013/0224143 A1 | 8/2013 | Sargent |
| 2013/0236413 A1 | 9/2013 | Sargent |
| 2015/0056255 A1 | 2/2015 | Ragot et al. |
| 2015/0071978 A1 | 3/2015 | Chang |
| 2015/0190450 A1 | 7/2015 | Chang |
| 2015/0328138 A1 | 11/2015 | Lo et al. |
| 2016/0283917 A1 | 9/2016 | Nunn et al. |
| 2017/0112742 A1 | 4/2017 | Turner |
| 2017/0137750 A1 | 5/2017 | Zhang et al. |
| 2018/0071201 A1 | 3/2018 | Aouad et al. |
| 2018/0133135 A1 | 5/2018 | Scheele et al. |
| 2018/0169000 A1 | 6/2018 | Park |
| 2019/0160022 A1 | 5/2019 | Chiou |
| 2020/0115506 A1 | 4/2020 | Aouad et al. |
| 2020/0163869 A1 | 5/2020 | McClendon |
| 2020/0281998 A1 | 9/2020 | Scharp et al. |
| 2020/0369986 A1 | 11/2020 | Hulskotter et al. |
| 2021/0000138 A1 | 1/2021 | Ambrogio et al. |
| 2022/0096334 A1 | 3/2022 | Deng et al. |

FOREIGN PATENT DOCUMENTS

| | | | |
|---|---|---|---|
| EP | 2314351 B1 | 12/2014 | |
| WO | WO 2010072577 A2 * | 7/2010 | ............... A61Q 5/10 |

OTHER PUBLICATIONS

"Hydra Source Dewy Moisture Mist for Dry Hair," Hydra Source Dewy Moisture Mist—Biolage, 2022, pp. 1-5.
"Be Gentle, Be Kind Aloe + Oat Milk Ultra Soothing Detangling Spray," Briogeo, 2022, pp. 1-5.
"Ceremonia—Oil Mist con Aloe Vera," Ceremonia—Oil Mist con Aloe Vera—Blue Hair Masks, Hair Care, 2022, pp. 1-6.

* cited by examiner

HAIR COLORING COMPOSITIONS AND METHODS

FIELD OF THE DISCLOSURE

The instant disclosure relates to hair coloring compositions comprising direct dyes, methods for coloring hair, and methods for making the hair coloring compositions.

SUMMARY

There are various methods for coloring hair depending on whether the color change should be permanent, semi-permanent, or temporary. Oxidative coloring procedures typically provide the longest lasting color change but can be complex and involve "chemically processing" the hair. The chemical processing improves color retention but can also alter other properties the hair. Semi-permanent and temporary coloring methods are simpler, do not require the same chemical processing, but are typically not long-lasting.

The hair coloring compositions of the instant disclosure are unique because they provide long-lasting color changes to hair without requiring chemical processing or complicated mixing and application procedures. For example, a consumer can apply the hair coloring compositions can directly to the hair "as-is," for example by spraying the compositions on the hair to be colored. The compositions effectively and immediately color the hair. In addition, the compositions also impart a conditioning-effect to the hair, resulting in soft, hydrated, and shiny look and feel. This sets the coloring compositions apart from other hair coloring compositions commonly used for coloring hair that can damage and dry the hair.

The hair coloring compositions of the instant disclosure include:
  (a) aloe barbadensis leaf juice;
  (b) one or more polyether-modified polysiloxanes;
  (c) one or more non-silicone nonionic surfactants selected from alkoxylated compounds;
  (d) one or more cationic surfactants;
  (e) optionally, one or more water-soluble organic solvents;
  (f) one or more direct dyes; and
  (g) water.

In various embodiments, the hair coloring compositions are a homogenous single-phase liquid. In other embodiments, the hair coloring composition is an emulsion or a dispersion.

The hair coloring compositions can easily be applied to the hair, for example, by spraying the composition onto the hair.

Nonlimiting examples of polyether-modified polysiloxanes include PEG/PPG-18/18 dimethicone, PEG-12 dimethicone, PEG-12 dimethicone, PEG-14 dimethicone, PEG/PPG-22/24 dimethicone, PEG/PPG-17/18 dimethicone, PEG/PPG-20/6 dimethicone, PEG/PPG-14/4 dimethicone, and mixtures thereof.

Nonlimiting examples of non-silicone nonionic surfactants include straight chain primary alcohol alkoxylates, straight chain secondary alcohol alkoxylates, alkyl phenol alkoxylates, olefinic alkoxylates, branched chain alkoxylates, fatty oil or hydrogenated fatty oil ethoxylates, alkyl sorbitan esters ethoxylates, alkyl glyceride ethoxylates, and mixtures thereof.

Nonlimiting examples of cationic surfactants include dialkyl dimonium halide compounds, for example, di-C12-15 alkyl dimonium chloride, C12-18 dialkyldimonium chloride, di-C12-18 alkyl dimonium chloride, dicapryl/dicaprylyl dimonium chloride, didecyldimonium chloride, dicetyldimonium chloride, ditallowdimonium chloride, dicocodimonium chloride, distearyldimonium chloride, ceteardimonium chloride, hydroxyethyl oleyl dimonium chloride, panthenyl hydroxypropyl steardimonium chloride, hydroxypropyl bis-hydroxyethyldimonium chloride, hydroxypropyl bisstearyldimonium chloride, hydroxycetyl hydroxyethyl dimonium chloride, hydroxyethyl behenamidopropyl dimonium chloride, behenamidopropyl PG-dimonium chloride, cocamidopropyl PG-dimonium chloride, oleamidopropyl PG-dimonium chloride, behentrimonium chloride, and mixtures thereof.

Nonlimiting examples of water-soluble organic solvents include glycerin, mono-alcohols, polyols (polyhydric alcohols), glycols, and a mixture thereof.

Nonlimiting examples of direct dyes include nitro-phenylenediamines, nitro-aminophenols, azo dyes, anthraquinones, triarylmethane dyes, indophenols, and a combination thereof. The direct dyes may be cationic, anionic, neutral, or combinations thereof. In certain embodiments, it is preferable to include at least one cationic direct dye.

In certain embodiments, the hair coloring composition includes one or more miscellaneous ingredients. Nonlimiting examples of miscellaneous ingredients include antioxidants, pH adjusters, salts, fragrances, preservatives, botanical extracts, chelating agents, vitamins, amino acids, cosmetic colorants, and mixtures thereof.

In certain embodiments, the hair coloring composition is free or essentially free of one or more components. For example, in various embodiments, the hair coloring composition is free or essentially free from amino silicones, for example, amodimethicone. In various embodiments, the hair coloring composition is free or essentially free from polyorganosiloxanes other than the polyether-modified polysiloxanes of (c). In various embodiments, the hair coloring composition is free or essentially free from oxidative dye precursors.

The instant disclosure further relates to methods for coloring hair. Such methods comprising applying a hair coloring composition according to the instant disclosure to the hair. The hair coloring composition can be applied to dry hair, wet hair, or damp hair. Furthermore, the hair coloring composition may be allowed to remain on the hair indefinitely without washing the hair or it may be allowed to remain on the hair for a minimum threshold amount of time before rinsing or washing the hair coloring compositions from the hair. The hair coloring compositions can be applied to the hair according to any method known in the art. Nonetheless, in certain embodiments, the hair coloring composition is conveniently applied to the hair by spraying the composition onto the hair.

BRIEF DESCRIPTION OF THE DRAWINGS

Implementation of the present technology is described, by way of example only, with reference to the attached figures, wherein.

Figure 1:
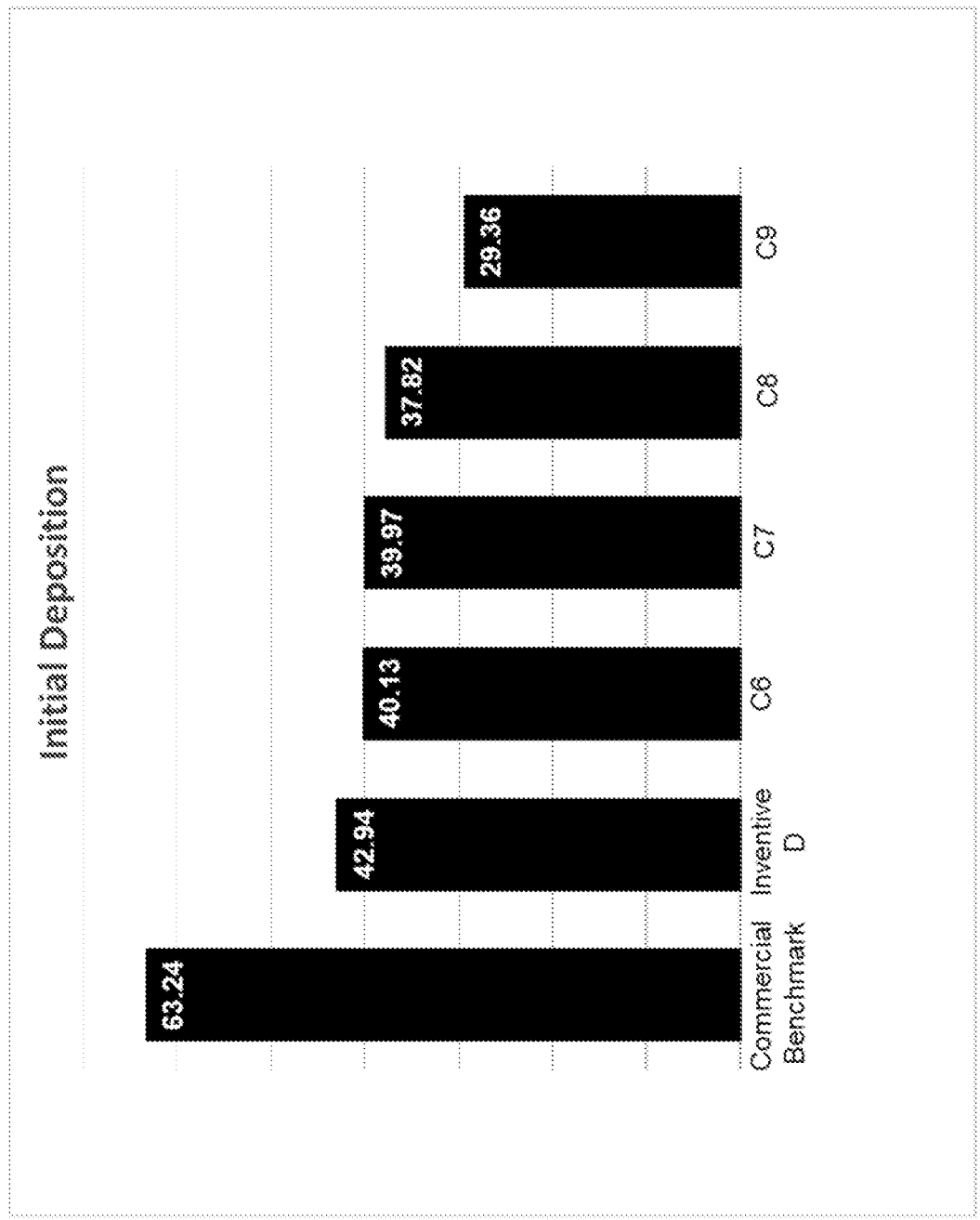
FIG. 1 reports the degree of color change of hair swatches after application of hair coloring compositions according to the instant disclosure.

It should be understood that the various aspects are not limited to the representations set forth in the drawings.

DETAILED DESCRIPTION

The hair coloring compositions of the instant disclosure provide long-lasting and durable color changes to hair. The compositions effectively and immediately color the hair but also impart a conditioning-effect to the hair, resulting in a soft, hydrated, and shiny look and feel.

In various embodiments, the hair coloring compositions of the instant disclosure comprise:
(a) about 1 to about 25 wt. %, preferably about 2 to about 20, more preferably about 5 to about 15 wt. % of aloe barbadensis leaf juice;
(b) about 1 to about 10 wt. %, preferably about 1 to about 8 wt. %, more preferably about 2 to about 6 wt. % of one or more polyether-modified polysiloxanes;
(c) about 0.5 to about 10 wt. %, preferably about 1 to about 6 wt. %, more preferably about 1.5 to about 5 wt. % of one or more non-silicone nonionic surfactants selected from alkoxylated compounds;
(d) about 0.05 to about 8 wt. %, more preferably about 0.1 to about 6 wt. %, more preferably about 0.1 to about 4 wt. % of one or more cationic surfactants;
(e) optionally, one or more water-soluble organic solvents;
(f) one or more direct dyes; and
(g) about 60 to about 92 wt. %, more preferably about 70 to about 90 wt. %, more preferably about 75 to about 90 wt. % of water;
wherein all weight percentages are based on the total weight of the hair coloring composition.

In various embodiments, the hair coloring compositions are homogenous single-phase liquid. In further embodiments, the coloring compositions are emulsions or dispersions. Regardless, the compositions can easily be applied to the hair, for example, by spraying the compositions onto the hair.

(a) Aloe Barbadensis Leaf Juice (Aloe Vera)

The coloring compositions include aloe barbadensis leaf juice, which provides a myriad of benefits to the compositions and contributes to the compositions' ability to nourish, hydrate, and condition hair. Aloe barbadensis is a succulent plant species. The aloe leaf can be divided into two major parts, namely the outer green rind, including the vascular bundles, and the inner colorless parenchyma containing the aloe gel. The inner central part of the aloe leaf is referred to by different terms that are used interchangeably such as inner pulp, mucilage tissue, mucilaginous gel, mucilaginous jelly, inner gel and leaf parenchyma tissue. Technically, the term 'pulp' or 'parenchyma tissue' refers to the intact fleshy inner part of the leaf including the cell walls and organelles, 'gel' or 'mucilage' refers to the viscous clear liquid within the parenchyma cells.

For purposes of the instant disclosure the terms "aloe barbadensis leaf juice" refers to the mucilage of the leaf. This definition, however, does not exclude other parts of the inner colorless parenchyma or even other parts of the leaf from inclusion in the instant compositions.

The total amount of the aloe barbadensis leaf juice in the compositions will vary. Nonetheless, in various embodiments, the total amount of the aloe barbadensis leaf juice in the compositions is from about 1 to about 25 wt. %, based on the total weight of the composition. In further embodiments, the total amount of the barbadensis leaf juice is from about 1 to about 20 wt. %, about 1 to about 15 wt. %, about 1 to about 12 wt. %, about 2 to about 25 wt. %, about 2 to about 20 wt. %, about 2 to about 15 wt. %, about 2 to about 12 wt. %, about 5 to about 25 wt. %, about 5 to about 20 wt. %, about 5 to about 15 wt. %, about 5 to about 12 wt. %, about 8 to about 20 wt. %, about 8 to about 15 wt. %, or about 8 to about 12 wt. %, based on the total weight of the composition.

(b) Polyether-Modified Polysiloxanes

Nonlimiting examples of polyether-modified polysiloxanes include compounds of the following formula.

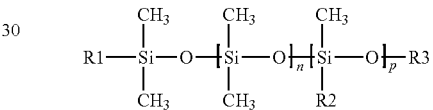

Radicals R1 and R3 independently constitute a hydrogen atom, an alkyl group with from about 1 to about 30 C-atoms, an alkoxy group with from about 1 to about 30 C-atoms or a possibly substituted phenyl group, Radical R2 constitutes the group $-C_cH_{2c}-O-(C_2H_4O-)_a(C_3H_6O-)_bR5$, Radical R5 constitutes a hydrogen atom or a linear or branched alkyl group with 1 to 16 C-atoms, $n$ is a number from about 0 to about 500,
$p$ is a number from about 1 to about 50,
$a$ is a number from about 0 to about 50,
$b$ is a number from about 0 to about 50,
$a+b$ are at least 1, and
$c$ is a number from about 1 to about 4.

In certain embodiments, polyether-modified polysiloxanes of the general structural formula (I) are:

TABLE 1

| | R1, R3 | R2 | R5 | n | p | a | b | c |
|---|---|---|---|---|---|---|---|---|
| 1 | H, methyl | $-C_cH_{2c}-O-(C_2H_4O)_a-(C_3H_6O)_b-R_5$ | H, methyl | 1-500 | 5-50 | 15-25 | 15-25 | 3 |
| 2 | H, methyl | $-C_cH_{2c}-O-(C_2H_4O)_a-(C_3H_6O)_b-R_5$ | H, methyl | 1-500 | 5-50 | 5-20 | 0.1 | 3 |
| 3 | H, methyl | $-C_cH_{2c}-O-(C_2H_4O)_a-(C_3H_6O)_b-R_5$ | H, methyl | 0.1 | 1-3 | 5-10 | 0.1 | 2 |
| 4 | H, methyl | $-C_cH_{2c}-O-(C_2H_4O)_a-(C_3H_6O)_b-R_5$ | H, methyl | 1-500 | 5-50 | 20-30 | 20-30 | 3 |
| 5 | H, methyl | $-C_cH_{2c}-O-(C_2H_4O)_a-(C_3H_6O)_b-R_5$ | H, methyl | 1-500 | 5-50 | 10-25 | 10-25 | 3 |
| 6 | H, methyl | $-C_cH_{2c}-O-(C_2H_4O)_a-(C_3H_6O)_b-R_5$ | H, methyl | 1-500 | 2-50 | 10-30 | 2-10 | 3 |
| 7 | H, methyl | $-C_cH_{2c}-O-(C_2H_4O)_a-(C_3H_6O)_b-R_5$ | H, methyl | 1-500 | 2-50 | 10-20 | 1-10 | 3 |

TABLE 2

| R1, R3 | R2 | R5 | n | p | a | b | c |
|---|---|---|---|---|---|---|---|
| 1 Methyl | —$C_cH_{2c}$—O—$(C_2H_4O)_a$—$(C_3H_6O)_b$—$R_5$ | H, methyl | 5-500 | 7-50 | 15-20 | 15-20 | 3 |
| 2 Methyl | —$C_cH_{2c}$—O—$(C_2H_4O)_a$—$(C_3H_6O)_b$—$R_5$ | H, methyl | 5-500 | 7-50 | 7-15 | 0 | 3 |
| 3 Methyl | —$C_cH_{2c}$—O—$(C_2H_4O)_a$—$(C_3H_6O)_b$—$R_5$ | H, methyl | 0.1 | 1 | 6-8 | 0 | 2 |
| 4 Methyl | —$C_cH_{2c}$—O—$(C_2H_4O)_a$—$(C_3H_6O)_b$—$R_5$ | H, methyl | 5-500 | 7-50 | 20-25 | 20-25 | 3 |
| 5 Methyl | —$C_cH_{2c}$—O—$(C_2H_4O)_a$—$(C_3H_6O)_b$—$R_5$ | H, methyl | 5-500 | 7-50 | 15-20 | 15-20 | 3 |
| 6 Methyl | —$C_cH_{2c}$—O—$(C_2H_4O)_a$—$(C_3H_6O)_b$—$R_5$ | H, methyl | 5-500 | 2-50 | 15-25 | 2-8 | 3 |
| 7 Methyl | —$C_cH_{2c}$—O—$(C_2H_4O)_a$—$(C_3H_6O)_b$—$R_5$ | H, methyl | 5-500 | 2-50 | 10-15 | 1-5 | 3 |

TABLE 3

| R1, R3 | R2 | R5 | n | p | a | b | c |
|---|---|---|---|---|---|---|---|
| 1 Methyl | —$C_cH_{2c}$—O—$(C_2H_4O)_a$—$(C_3H_6O)_b$—$R_5$ | Methyl | 10-500 | 10-50 | 18 | 18 | 3 |
| 2 Methyl | —$C_cH_{2c}$—O—$(C_2H_4O)_a$—$(C_3H_6O)_b$—$R_5$ | Methyl | 10-500 | 10-50 | 12 | 0 | 3 |
| 3 Methyl | —$C_cH_{2c}$—O—$(C_2H_4O)_a$—$(C_3H_6O)_b$—$R_5$ | Methyl | 10-500 | 10-50 | 14 | 0 | 3 |
| 4 Methyl | —$C_cH_{2c}$—O—$(C_2H_4O)_a$—$(C_3H_6O)_b$—$R_5$ | Methyl | 0 | 1 | 7 | 0 | 2 |
| 5 Methyl | —$C_cH_{2c}$—O—$(C_2H_4O)_a$—$(C_3H_6O)_b$—$R_5$ | Methyl | 10-500 | 10-50 | 22 | 24 | 3 |
| 6 Methyl | —$C_cH_{2c}$—O—$(C_2H_4O)_a$—$(C_3H_6O)_b$—$R_5$ | Methyl | 10-500 | 10-50 | 17 | 18 | 3 |
| 7 Methyl | —$C_cH_{2c}$—O—$(C_2H_4O)_a$—$(C_3H_6O)_b$—$R_5$ | Methyl | 10-500 | 5-50 | 20 | 6 | 3 |
| 8 Methyl | —$C_cH_{2c}$—O—$(C_2H_4O)_a$—$(C_3H_6O)_b$—$R_5$ | Methyl | 10-500 | 5-50 | 14 | 4 | 3 |

Polyether-modified polysiloxane compounds listed in the above Tables 1-3, are commercially available under the following trade names, for example:

DOW CORNING 190 (INCI: PEG/PPG-18/18 Dimethicone),

DOW CORNING 193 (INCI: PEG-12 Dimethicone),

ABIL® B 8843 (INCI: PEG-14 Dimethicone),

SILWET L-77 (INCI: Siloxane Polyalkyleneoxide Copolymer),

MIRASIL DCMO (INCI: Cyclomethicone, PEG/PPG-22/24 Dimethicone),

DOW CORNING Q2-5220 (INCI: PEG/PPG-17/18 Dimethicone),

ABIL® B 88184 (INCI: PEG/PPG-20/6 Dimethicone), and

ABIL® B 8851 (INCI: PEG/PPG-14/4 Dimethicone).

In various embodiments, the one or more polyether-modified polysiloxanes are chosen from PEG/PPG-18/18 dimethicone, PEG-12 dimethicone, PEG-14 dimethicone, siloxane polyalkyleneoxide copolymer, PEG/PPG-22/24 dimethicone, PEG/PPG-17/18 dimethicone, PEG/PPG-20/6 dimethicone, PEG/PPG-14/4 dimethicone, and mixtures thereof, preferably chosen from PEG-12 dimethicone, PEG-14 dimethicone, and a mixture thereof.

The total amount of the one or more polyether-modified polysiloxanes in the compositions will vary. Nonetheless, in various embodiments, the total amount of the one or more polyether-modified polysiloxanes is from about 1 to about 10 wt. %, based on the total weight of the composition. In further embodiments, the total amount of the one or more polyether-modified polysiloxanes in the compositions is from about 1 to about 8 wt. %, about 1 to about 6 wt. %, about 1 to about 5 wt. %, about 2 to about 10 wt. %, about 2 to about 8 wt. %, about 2 to about 6 wt. %, about 2 to about 5 wt. %, about 2 to about 4 wt. %, or about 2 to about 3 wt. %, based on the total weight of the composition.

(c) Non-Silicone Nonionic Surfactants Selected from Alkoxylated Compounds

The non-silicone nonionic surfactants may comprise an average of from 2 to 100 moles of alkylene oxide per mole of the nonionic surfactant. This is referred to herein as the alkoxylation number (of the non-silicone nonionic surfactant). Nonlimiting examples of non-silicone nonionic surfactants include addition products of ethylene oxide and/or propylene oxide with fatty alcohols, fatty acids, fatty amines and fatty oils. Suitable non-silicone nonionic surfactants include surfactants of the general formula: R—Y—$(C_2H_4O)_z$—$C_2H_4OH$ where R is selected from the group consisting of primary, secondary and branched chain alkyl and/or acyl hydrocarbyl groups; primary, secondary and branched chain alkenyl hydrocarbyl groups; and primary, secondary and branched chain alkenyl-substituted phenolic hydrocarbyl groups; the hydrocarbyl groups having a chain length of from 8 to about 25, preferably 10 to 20, e.g., 14 to 18 carbon atoms. R may also be mono-, di-, or tri-alkyl glycerides with hydroxyl group as side group in each of the alkyl chains, for example, castor oil or hydrogenated castor oil. R may also be alkyl sorbitan esters, with the carbon chain length of from 8 to 25.

In the general formula for the ethoxylated nonionic surfactant, Y is typically: —O—, —C(O)O—, —C(O)N(R)—, or —C(O)N(R)R—; wherein R has the meaning given above or can be hydrogen; and Z is at least 1, preferably from 10 to 100, 10 to 80, or 10-60. Preferably the nonionic surfactant has an HLB of from 3 to 20, more preferably from 10 to 18, e.g. 12 to 16.

Nonlimiting examples of non-silicone nonionic surfactants are as follows. In the examples, the integer defines the number of ethoxy (EO) groups in the molecule.

(i) Straight-Chain, Primary Alcohol Alkoxylates

Examples are the deca-, undeca-, dodeca-, tetradeca-, and pentadecaethoxylates of n-hexadecanol, and n-octadecanol having an HLB within the range recited herein. The ethoxylates of mixed natural or synthetic alcohols in the "tallow" chain length range are also useful herein. Specific examples of such materials include tallow alcohol-EO(11), tallow alcohol-EO(18), and tallow alcohol-EO (25).

(ii) Straight-Chain, Secondary Alcohol Alkoxylates

Examples are the deca-, undeca-, dodeca-, tetradeca-, pentadeca-, octadeca-, and nonadeca-ethoxylates of 3-hexadecanol, 2-octadecanol, 4-eicosanol, and 5-eicosanol having an HLB within the range recited herein.

(iii) Alkyl Phenol Alkoxylates

As in the case of the alcohol alkoxylates, examples are the hexa- to octadeca-ethoxylates of alkylated phenols, particularly monohydric alkylphenols, having an HLB within the range recited herein. The hexa- to octadeca-ethoxylates of p-tri-decylphenol, m-pentadecylphenol, and the like, are useful herein.

As used herein and as generally recognized in the art, a phenylene group in the nonionic formula is the equivalent of an alkylene group containing from 2 to 4 carbon atoms. For present purposes, nonionics containing a phenylene group are considered to contain an equivalent number of carbon atoms calculated as the sum of the carbon atoms in the alkyl group plus about 3.3 carbon atoms for each phenylene group.

(iv) Olefinic Alkoxylates

Examples are the alkenyl alcohols, both primary and secondary, and alkenyl phenols corresponding to those disclosed immediately hereinabove can be ethoxylated to an HLB within the range recited herein.

(v) Branched Chain Alkoxylates

Branched chain primary and secondary alcohols which are available from the well-known "OXO" process can be ethoxylated and employed. The average alkoxylation number is from 10 to 40, more preferably from 10 to 30, most preferably from 10 to 20 (e.g. 11 to 19). Examples of commercially available alkoxylated nonionic alcohols include: LUTENSOL AT11 ($C_{16-18}$ fatty alcohol 11 EO); LUTENSOL A8 ($C_{12-14}$ fatty alcohol 8EO) and LUTENSOL AT 25 ($C_{16-18}$ fatty alcohol 25EO), all ex BASF; GENAPOL C050 (coco alcohol 5EO); GENAPOL C100 (coco alcohol 10EO); GENAPOL C200 (coco alcohol 20EO) and GENAPOL T-150 (tallow alcohol 15EO), all ex Clariant; and REMCOPAL 20, ex Elf Atochem (lauryl alcohol 19EO).

(vi) Fatty Oil or Hydrogenated Fatty Oil Ethoxylates

Examples of commercially available fatty oil ethoxylates are: ALKAMULS castor oil CRH/40C (PEG-40 hydrogenated castoroil), ALKAMULS EL 620 (PEG-30), Super Sterol Ester (C10-30 Cholesterol/Lanosterol Esters), Aqualose L30 (PEG-30 Lanolin).

(vii) Alkyl Sorbitan Esters Ethoxylates or Alkyl Glyceride Ethoxylates

Examples of commercially available fatty oil ethoxylates are: ALKAMULS PSML20 (Polysorbate 20), Glycerox HE (PEG-7 Glyceryl Cocoate).

The total amount of the one or more non-silicone nonionic surfactants selected from alkoxylated compounds in the compositions will vary. Nonetheless, in various embodiments, the total amount of the one or more non-silicone nonionic surfactants selected from alkoxylated compounds is from about 0.5 to about 10 wt. %, based on the total weight of the composition. In further embodiments, the total amount of the one or more non-silicone nonionic surfactants selected from alkoxylated compounds in the composition is from about 0.5 to about 8 wt. %, about 0.5 to about 6 wt. %, about 0.5 to about 5 wt. %, about 0.5 to about 4 wt. %, about 1 to about 10 wt. %, about 1 to about 8 wt. %, about 1 to about 6 wt. %, about 1 to about 5 wt. %, about 1 to about 4 wt. %, about 1 to about 3 wt. %, about 1 to about 2 wt. %, 1.5 to about 10 wt. %, about 1.5 to about 8 wt. %, about 1.5 to about 6 wt. %, about 1.5 to about 5 wt. %, about 1.5 to about 4 wt. %, or about 1.5 to about 3 wt. %, based on the total weight of the composition.

A more exhaustive but nonlimiting list of general nonionic surfactants is provided under the heading "Nonionic Surfactants Generally." The list includes various examples of non-silicone nonionic surfactants selected from alkoxylated compounds, useful as component (e). The list also includes non-alkoxylated nonionic surfactants, which can optionally be included in the hair coloring compositions of the instant case in addition to the non-silicone nonionic surfactants selected from alkoxylated compounds. Thus, in various embodiments, the hair coloring compositions include one or more non-silicone nonionic surfactants selected from alkoxylated compounds (component (e)) and optionally, one or more additional nonionic surfactants other than the one or more non-silicone nonionic surfactants selected from alkoxylated compounds (component (e)).

If present, the amount of the one or more nonionic surfactants other than the non-silicone nonionic surfactants selected from alkoxylated compounds (component (e)) will vary. Nonetheless, in certain embodiments, the hair coloring compositions include one or more nonionic surfactants other than the non-silicone nonionic surfactants selected from alkoxylated compounds (component (e)) in an amount from about 0.01 to about 6 wt. %, about 0.01 to about 5 wt. %, about 0.01 to about 3 wt. %, about 0.1 to about 6 wt. %, about 0.1 to about 5 wt. %, about 0.1 to about 3 wt. %, or about 0.1 to about 2 wt. %.

(d) Cationic Surfactants

The term "cationic surfactant" as defined by the instant disclosure as a surfactant that may be positively charged when it is contained in the hair coloring compositions.

The cationic surfactant may bear one or more positive permanent charges or may contain one or more functional groups that are cationizable in the composition according to the disclosure.

Non-limiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof, di-C12-15 alkyl dimonium chloride, C12-18 dialkyldimonium chloride, di-C12-18 alkyl dimonium chloride, dicapryl/dicaprylyl dimonium chloride, didecyldimonium chloride, dicetyldimonium chloride, ditallowdimonium chloride, dicocodimonium chloride, distearyldimonium chloride, ceteardimonium chloride, hydroxyethyl oleyl dimonium chloride, panthenyl hydroxypropyl steardimonium chloride, hydroxypropyl bis-hydroxyethyldimonium chloride, hydroxypropyl bisstearyldimonium chloride, hydroxycetyl hydroxyethyl dimonium chloride, hydroxyethyl behenamidopropyl dimonium chloride, behenamidopropyl PG-dimonium chloride, cocamidopropyl PG-dimonium chloride, oleamidopropyl PG-dimonium chloride, behentrimonium chloride, and mixtures thereof.

In some embodiments, the cationic surfactant is selected from cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and mixtures thereof.

In some embodiments, the cationic surfactant comprises cetrimonium chloride, behentrimonium chloride, and mixtures thereof.

Additional nonlimiting examples of cationic surfactants include behenalkonium chloride, benzethonium chloride, cetylpyridinium chloride, behentrimonium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium-5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, and hexadecyltrimethyl ammonium bromide.

The cationic surfactant(s) may also be chosen from optionally polyoxyalkylenated, primary, secondary or tertiary fatty amines, or salts thereof, and quaternary ammonium salts, and mixtures thereof.

In some cases, it is useful to use salts such as chloride salts of the quaternary ammonium compounds.

The fatty amines generally comprise at least one $C_8$-$C_{30}$ hydrocarbon-based chain.

Examples of quaternary ammonium salts that may especially be mentioned include: those corresponding to the general formula below:

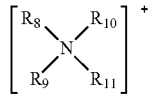

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and, in some embodiments, from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyal, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts of formula (III), those that are preferred are, on the one hand, tetraalkylammonium salts, for instance dialkyldimethylammonium or alkyltrimethylammonium salts in which the alkyl group contains approximately from 12 to 22 carbon atoms, in particular behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

Also useful are quaternary ammonium salts of imidazoline, such as, for example, those of formula below:

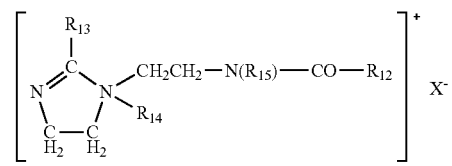

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a $C_1$-$C_4$ alkyl group, $X^-$ is an anion chosen from the group of halides, phosphates, acetates, lactates, alkyl sulfates, alkyl- or alkylarylsulfonates in which the alkyl and aryl groups, in some embodiments, comprise, respectively, from 1 to 20 carbon atoms and from 6 to 30 carbon atoms. $R_{12}$ and $R_{13}$, in some embodiments, denote a mixture of alkenyl or alkyl groups containing from 12 to 21 carbon atoms, derived for example from tallow fatty acids, $R_{14}$, in some embodiments, denotes a methyl group, and $R_{15}$, in some embodiments, denotes a hydrogen atom. Such a product is sold, for example, under the name REWOQUAT W 75 by the company Rewo.

Useful quaternary diammonium or triammonium salts includes those of the formula:

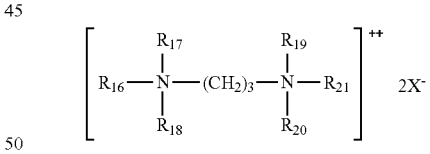

in which $R_{16}$ denotes an alkyl radical comprising approximately from 16 to 30 carbon atoms, which is optionally hydroxylated and/or interrupted with one or more oxygen atoms, $R_{17}$ is chosen from hydrogen or an alkyl radical comprising from 1 to 4 carbon atoms or a group $(R_{16a})(R_{17a})(R_{18a})N$—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms, and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75).

Useful cationic/cationizable surfactants, including cationizable surfactants together with an acid neutralizer, include those of the general structure R4-A-R5-B wherein $R_4$ is a saturated or unsaturated, straight or branched alkyl chain with 8 to 24 C atoms, $R_5$ is a straight or branched alkyl chain with 1 to 4 C atoms, A is selected from:

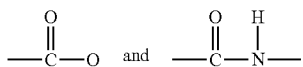

and B is selected from

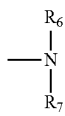

wherein $R_6$ and $R_7$ are the same or different is H or an alkyl chain with 1 to 4 C atoms, hydroxyl alkyl chain with 1 to 4 C atoms and di hydroxyl alkyl chain with 2 to 4 C atoms, and

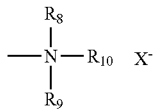

wherein $R_8$ and $R_9$ are the same or different, an alkyl chain with 1 to 4 C atoms, hydroxyl alkyl chain with 1 to 4 C atoms and di hydroxyl alkyl chain with 2 to 4 C atoms, R.sub.10 is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24C atoms, in some embodiments, 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, stearamidopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants may be chosen from fatty alkylamines and fatty dialkylamines. In some cases, the fatty dialkylamines may be fatty dimethylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used in the hair coloring compositions. In some instances, such non-polymeric mono-, di-, and/or tri-carboxylic acids can act to "neutralize" a fatty dialkylamine, if present. Non-limiting examples of di-carboxylic acids include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. A non-limiting example of a tri-carboxylic acid include citric acid. In certain embodiments, the hair coloring compositions preferably includes citric acid.

In preferred embodiments, at least one of the one or more cationic surfactants is a dialkyl dimonium compound, preferably a dialkyl dimonium halide compound. Non-limiting examples of dialkyl dimonium compounds include di-C12-15 alkyl dimonium chloride, C12-18 dialkyldimonium chloride, di-C12-18 alkyl dimonium chloride, dicapryl/dicaprylyl dimonium chloride, didecyldimonium chloride, dicetyldimonium chloride, ditallowdimonium chloride, dicocodimonium chloride, distearyldimonium chloride, ceteardimonium chloride, hydroxyethyl oleyl dimonium chloride, panthenyl hydroxypropyl steardimonium chloride, hydroxypropyl bis-hydroxyethyldimonium chloride, hydroxypropyl bisstearyldimonium chloride, hydroxycetyl hydroxyethyl dimonium chloride, hydroxyethyl behenamidopropyl dimonium chloride, behenamidopropyl PG-dimonium chloride, cocamidopropyl PG-dimonium chloride, oleamidopropyl PG-dimonium chloride, behenamidopropyl ethyldimonium ethosulfate, cocoamidopropyl ethyldimonium ethosulfate, dicetyldimonium chloride hydroxyethyl behenamidopropyl dimonium chloride, PEG-2-cocomonium chloride, PPG-9 diethylmonium chloride, PPG-25 diethylmonium chloride, PPG-40 diethylmonium chloride, stearamidopropyl ethyl dimonium ethosulfate, steardimonium hydroxypropyl hydrolyzed wheat protein, steardimonium hydroxypropyl hydrolyzed collagen, wheat germamidopropalkonium chloride, wheat germamidopropyl ethyldimonium ethosulfate, and mixtures thereof.

In various embodiments, at least one of the one or more of the cationic surfactants is a dialkyl dimonium halide compound chosen from di-C12-15 alkyl dimonium chloride, C12-18 dialkyldimonium chloride, di-C12-18 alkyl dimonium chloride, dicapryl/dicaprylyl dimonium chloride, didecyldimonium chloride, dicetyldimonium chloride, ditallowdimonium chloride, dicocodimonium chloride, distearyldimonium chloride, ceteardimonium chloride, hydroxyethyl oleyl dimonium chloride, panthenyl hydroxypropyl steardimonium chloride, hydroxypropyl bis-hydroxyethyldimonium chloride, hydroxypropyl bisstearyldimonium chloride, hydroxycetyl hydroxyethyl dimonium chloride, hydroxyethyl behenamidopropyl dimonium chloride, behenamidopropyl PG-dimonium chloride, cocamidopropyl PG-dimonium chloride, oleamidopropyl PG-dimonium chloride, behentrimonium chloride, and mixtures thereof.

In a preferred embodiment, the hair coloring compositions includes hydroxyethyl oleyl dimonium chloride.

The total amount of the one or more cationic surfactants in the compositions will vary. Nonetheless, in various embodiments, the total amount of the one or more cationic surfactants is from about 0.5 to about 8 wt. %, based on the total weight of the composition. In further embodiments, the total amount of the one or more cationic surfactants is from about 0.5 to about 6 wt. %, about 0.5 to about 5 wt. %, about 0.5 to about 4 wt. %, about 0.5 to about 3 wt. %, about 0.1 to about 8 wt. %, about 0.1 to about 6 wt. %, about 0.1 to about 5 wt. %, about 0.1 to about 4 wt. %, about 0.1 to about 3 wt. %, or about 0.1 to about 2 wt. %, based on the total weight of the composition.

(e) Water-Soluble Organic Solvents

The term "water-soluble solvent" is interchangeable with the term "water-miscible solvent" and relates to organic compounds that are liquid at 25° C. and at atmospheric pressure (760 mmHg), and have a solubility of at least 50% in water under these conditions. In some cases, the water-soluble solvent has a solubility of at least 60%, 70%, 80%, or 90%. Non-limiting examples of water-soluble solvents include, for example, glycerin, alcohols (for example, $C_{1-15}$, $C_{1-10}$, or $C_{1-4}$ alcohols), organic solvents, polyols (polyhydric alcohols), glycols (e.g., butylene glycol, caprylyl glycol, etc.), and a mixture thereof.

Non-limiting examples of water-soluble solvents include monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of are ethylene glycol, propylene glycol, butylene glycol, hexylene glycol, propane diol, and glycerin. The organic solvents can be volatile or non-volatile compounds.

Further non-limiting examples of water-soluble solvents include alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some instances, polyhydric alcohols may be particularly useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

In a preferred embodiment, the hair treatment compositions include one or more water-soluble solvents chosen from chosen glycerin, $C_{1-6}$ mono-alcohols, polyols (polyhydric alcohols), glycols, and a mixture thereof. In an even more preferred embodiment, the hair treatment compositions include one or more water-soluble solvents chosen from glycerin, propylene glycol, butylene glycol, pentylene glycol, hexylene glycol, dipropylene glycol, and mixtures thereof.

The total amount of the one or more water-soluble organic solvents in the composition, if present, will vary. Nonetheless, in various embodiments, the total amount of the one or more water-soluble organic solvents, if present, is from about 0.1 to about 25 wt. %, based on the total weight of the compositions. In further embodiments, the total amount of the one or more water-soluble organic solvents is from about 0.1 to about 20 wt. %, about 0.1 to about 15 wt. %, about 0.1 to about 10 wt. %, about 0.1 to about 5 wt. %, about 0.5 to about 25 wt. %, about 0.5 to about 20 wt. %, about 0.5 to about 15 wt. %, about 0.5 to about 10 wt. %, about 0.5 to about 5 wt. %, about 1 to about 25 wt. %, about 1 to about 20 wt. %, about 1 to about 15 wt. %, about 1 to about 10 wt. %, about 1 to about 5 wt. %, based on the total weight of the composition.

(f) Direct Dyes

A direct dye is a colored substance that does not require the use of an oxidizing agent in order to reveal its color on hair. Suitable direct dyes that may be used in the hair coloring compositions may include or be chosen from acidic (anionic), basic (cationic), and neutral dyes.

"Acidic dye" is generally intended to mean a dye containing at least one COOH, $SO_3H$, $PO_3H$, or $PO_4H_2$ group, it being possible for said groups to exist in the form of salts. "Salts" is generally intended to mean salts of metals (for example, alkali metals or alkaline earth metals), salts of an organic amine that may optionally be hydroxylated.

Such dyes are also referred to as anionic dyes. Exemplary acidic dyes that may be suitably used in the hair coloring compositions include or can be chosen from acidic nitro dyes, acidic azo dyes, acidic azine dyes, acidic triarylmethane dyes, acidic quinone dyes, acidic indo-amine dyes and acidic natural dyes, and mixtures thereof.

"Basic dyes" is generally intended to mean a dye that has at least one group bearing a positive charge, such as an ammonium group or a quaternized nitrogen atom in a ring. Such dyes are also referred to as cationic dyes. Suitable basic dyes that may be used in hair coloring compositions include and/or can be chosen from nitrobenzene dyes, azo dyes, azomethine dyes, methine dyes, tetraazapentamethine dyes, anthraquinone dyes, naphthoquinone dyes, benzoquinone dyes, phenothiazine dyes, indigoid dyes, xanthene dyes, phenanthridine dyes, phthalocyanin dyes, triarylamethane-derived dyes and basic natural dyes, and mixtures thereof.

Examples of suitable direct dyes that may be mentioned include azo direct dyes; anthraquinone and anthraquinone derivatives; (poly)methine dyes such as cyanins, hemicyanins and styryls; carbonyl dyes; azine dyes; nitro(hetero)aryl dyes; tri(hetero)arylmethane dyes; porphyrin dyes; phthalocyanin dyes, and natural direct dyes, alone or as mixtures. The direct dyes may be cationic or anionic.

Many direct dyes are cationic direct dyes. Mention may be made of the hydrazono cationic dyes of formulas (Va) and (V'a), the azo cationic dyes (VIa) and (VI'a) and the diazo cationic dyes (VIIa) below:

| | |
|---|---|
| $Het^+$—$C(R^a)$=N—$N(R^b)$—Ar, $An^-$ | (Va) |
| $Het^+$—$N(R^a)$—N=$C(R^b)$—Ar, $An^-$ | (V'a) |
| $Het^+$—N=N—Ar, $An^-$ | (VIa) |
| $Ar^+$—N=N—Ar'', $An^-$ | (VI'a) and |
| $Het^+$—N=N—Ar'—N=N—Ar, $An^-$ | (VIIa) | in which formulas (Va), (V'a), (VIa), (VI'a) and (VIIa):

$Het^+$ represents a cationic heteroaryl radical, preferably bearing an endocyclic cationic charge, such as imidazolium, indolium or pyridinium, optionally substituted preferentially with one or more $(C_1-C_8)$ alkyl groups such as methyl;

$Ar^+$ representing an aryl radical, such as phenyl or naphthyl, bearing an exocyclic cationic charge, preferentially ammonium, particularly tri$(C_1-C_8)$alkylammonium such as trimethylammonium;

Ar represents an aryl group, especially phenyl, which is optionally substituted, preferentially with one or more electron-donating groups such as i) optionally substituted $(C_1-C_8)$alkyl, ii) optionally substituted $(C_1-C_8)$alkoxy, iii) (di)$(C_1-C_8)$(alkyl)amino optionally substituted on the alkyl group(s) with a hydroxyl group, iv) aryl$(C_1-C_8)$alkylamino, v) optionally substituted N—$(C_1-C_8)$alkyl-N-aryl$(C_1-C_8)$alkylamino or alternatively Ar represents a julolidine group;

Ar' is an optionally substituted divalent (hetero)arylene group such as phenylene, particularly para-phenylene, or naphthalene, which are optionally substituted, preferentially with one or more groups $(C_1-C_8)$alkyl, hydroxyl or $(C_1-C_8)$alkoxy Ar'' is an optionally substituted (hetero)aryl group such as phenyl or pyrazolyl, which are optionally substituted, preferentially with one or more groups $(C_1-C_8)$alkyl, hydroxyl, (di)$(C_1-C_8)$(alkyl)amino, $(C_1-C_8)$alkoxy or phenyl;

$R^a$ and $R^b$, which may be identical or different, represent a hydrogen atom or a group $(C_1-C_8)$alkyl, which is optionally substituted, preferentially with a hydroxyl group;

or alternatively the substituent $R^a$ with a substituent of $Het^+$ and/or $R_b$ with a substituent of Ar and/or $R^a$ with $R_b$ form, together with the atoms that bear them, a (hetero)cycloalkyl;

particularly, $R^a$ and $R_b$ represent a hydrogen atom or a group $(C_1-C_4)$alkyl, which is optionally substituted with a hydroxyl group;

$An^-$ represents an anionic counter-ion such as mesylate or halide. In particular, mention may be made of the azo and hydrazono cationic dyes bearing an endocyclic cationic charge of formulae (Va), (V'a) and (VIa) as defined previously. More particularly those of formulae (Va), (V'a) and (VIa) derived from the dyes described in patent applications WO 95/15144, WO 95/01772 and EP-714954, which are incorporated herein by reference in their entirety.

In some cases, the cationic part is derived from the following derivatives:

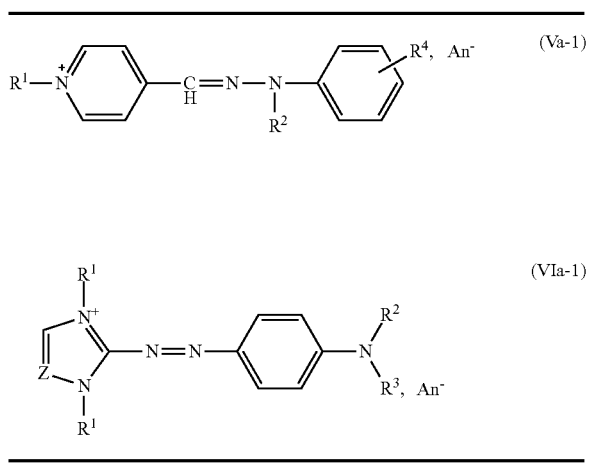

formulae (V-1) and (VI-1) with:

$R^1$ representing a ($C_1$-$C_4$) alkyl group such as methyl;

$R^2$ and $R^3$, which are identical or different, represent a hydrogen atom or a ($C_1$-$C_4$)alkyl group, such as methyl; and $R^4$ represents a hydrogen atom or an electron-donating group such as optionally substituted ($C_1$-$C_8$)alkyl, optionally substituted ($C_1$-$C_8$)alkoxy, or (di)($C_1$-$C_8$) (alkyl)amino optionally substituted on the alkyl group(s) with a hydroxyl group; particularly, $R^4$ is a hydrogen atom, Z represents a CH group or a nitrogen atom, preferentially CH;

An⁻ represents an anionic counter-ion such as mesylate or halide.

Particularly, the dye of formulae (Va-1) and (VIa-1) is chosen from Basic Red 51, Basic Yellow 87 and Basic Orange 31 or derivatives thereof:

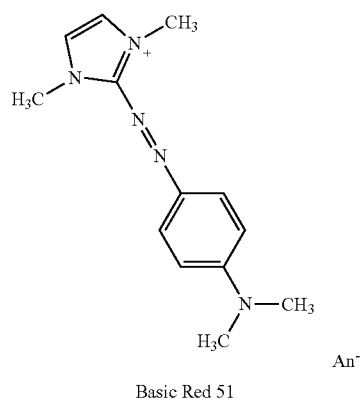

Basic Red 51

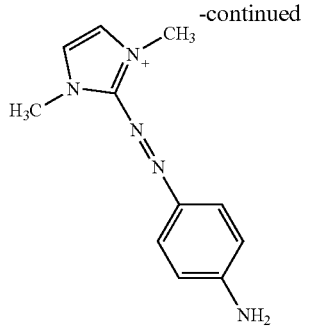

Basic Orange 31

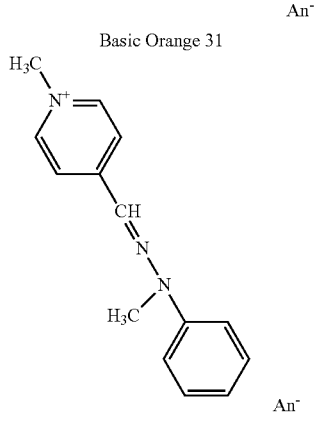

Basic Yellow 87

Non-limiting examples of cationic dyes include Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87.

Non-limiting examples anionic dyes include Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2 (Ext Violet 2), D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium and/or potassium.

Non-limiting examples of nitro dyes include HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Blue No. 17, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No.

2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

In various embodiments, at least one of the one or more direct dyes include at least one halogenated aromatic ring. There are various classes of direct dyes that can include a halogenated aromatic ring, for example, triarylmethane dyes, xanthene dyes, azo dyes, etc., and mixtures thereof. Nonlimiting examples of xanthene dyes comprising at least one halogenated aromatic ring include D&C Red 28, D&C Red 27, Eosin Y, Eosin B, Erythrosine B, Rose Bengal, etc. Nonlimiting examples of triarylmethane dyes comprising at least one halogenated aromatic ring include Tetrabromophenol Blue, Tetrabromo-sulfonephthalein, Bromsulphthalein, Bromocresol Green, Bromothymol Blue, etc. Nonlimiting examples of azo dyes comprising at least one halogenated aromatic ring include Acid Red 337, Disperse Red 167, Basic Red 18, Disperse Red 118, etc.

In a preferred embodiment, at least one of the one or more direct dyes is a cationic direct dye.

The hair coloring compositions of the instant disclosure do not require oxidizing agents. Thus, the hair coloring compositions may optionally be free or essentially free from oxidizing agents. Nonlimiting examples of oxidizing agents include hydrogen peroxide, inorganic alkali metal peroxides, organic peroxides, inorganic perhydrate salts, bromates, and a mixture thereof.

The total amount of the one or more direct dyes in the composition will vary. Nonetheless, in various embodiments, the total amount of the one or more direct dyes in the composition is from about 0.0001 to about 5 wt. % based on the total weight of the developer composition. In further embodiments, the total amount of the one or more direct dyes comprising at least one halogenated aromatic ring in the developer composition is from about 0.0001 to about 4 wt. %, about 0.0001 to about 3 wt. %, about 0.0001 to about 2 wt. %, about 0.0001 to about 1 wt. %, about 0.0001 to about 0.5 wt. %, about 0.0005 to about 4 wt. %, about 0.0005 to about 3 wt. %, about 0.0005 to about 2 wt. %, about 0.0005 to about 1 wt. %, about 0.0005 to about 0.5 wt. %, about 0.001 to about 5 wt. %, about 0.001 to about 4 wt. %, about 0.001 to about 3 wt. %, about 0.001 to about 2 wt. %, about 0.001 to about 1 wt. %, about 0.010 to about 0.5 wt. %, about 0.1 to about 4 wt. %, about 0.1 to about 4 wt. %, about 0.1 to about 3 wt. %, about 0.1 to about 2 wt. %, or about 0.1 to about 1 wt. %, based on the total weight of the composition.

(g) Water

For purposes of this disclosure, the amount of water referred to herein is all water in the composition except for the water present in the aloe barbadensis leaf juice. Aloe barbadensis leaf juice naturally includes water, which forms part of the aloe barbadensis leaf juice. If a composition according to the instant disclosure includes about 10 wt. % of aloe barbadensis leaf juice, a portion of the about 10 wt. % of aloe barbadensis leaf juice may be water. However, because this water is part of the aloe barbadensis leaf juice, it is not included in the total amount of "water" referenced throughout the disclosure. The amount of water (i.e., the total amount of water other than the water present in the aloe barbadensis leaf juice) in the compositions will vary. Nonetheless, in various embodiments, the total amount of water in the composition (i.e., the total amount of water other than the water present in the aloe barbadensis leaf juice) is from about 60 to about 92 wt. %, based on the total weight of the composition. In further embodiments, the total amount of water (i.e., the total amount of water other than the water present in the aloe barbadensis leaf juice) in the composition is from about 65 to about 92 wt. %, about 70 to about 92 wt. %, about 75 to about 92 wt. %, about 80 to about 92 wt. %, about 60 to about 90 wt. %, about 65 to about 90 wt. %, about 70 to about 90 wt. %, about 75 to about 90 wt. %, about 80 to about 90 wt. %, about 60 to about 85 wt. %, about 65 to about 85 wt. %, about 70 to about 85 wt. %, about 75 to about 85 wt. %, or about 80 to about 85 wt. %, based on the total weight of the composition.

(h) Miscellaneous Ingredients

The compositions the instant disclosure may optionally include (or optionally exclude) one more miscellaneous ingredients. Miscellaneous ingredients are ingredients that are compatible with the hair coloring compositions and do not disrupt or materially affect the basic and novel properties of the compositions. Nonlimiting examples of ingredients include preservatives, fragrances, pH adjusters, salts, chelating agents, buffers, antioxidants, flavonoids, vitamins, botanical extracts, UV filtering agents, proteins, protein hydrolysates, and/or isolates, fillers (e.g., organic and/or inorganic fillers such as talc, calcium carbonate, silica, etc.) composition colorants, cationic polymers, thickening agents, etc. In various embodiments, the miscellaneous ingredients are chosen from preservatives, fragrances, pH adjusters, salts, chelating agents, buffers, composition colorants, and mixtures thereof. In the context of the instant disclosure, a "composition colorant" is a compound that colors the composition but does not have an appreciable coloring effect on hair. In other words, the composition colorant is included to provide a coloring to the composition for aesthetic appeal but is not intended to impart coloring properties to hair. Styling gels, for example, can be found in a variety of different colors (e.g., light blue, light pink, etc.) yet application of the styling gel to hair does not visibly change the color of the hair.

The total amount of the one or more miscellaneous ingredients, if present, will vary. Nonetheless, in various embodiments, the compositions of the instant disclosure include from about 0.001 to about 10 wt. % of one or more miscellaneous ingredients, based on the total weight of the composition. In further embodiments, the compositions of the instant disclosure include from about 0.001 to about 5 wt. %, about 0.001 to about 3 wt. %, about 0.01 to about 10 wt. %, about 0.01 to about 5 wt. %, about 0.01 to about 3 wt. %, about 0.1 to about 10 wt. %, about 0.1 to about 5 wt. %, or about 0.1 to about 3 wt. % of one or more miscellaneous ingredients, based on the total weight of the composition.

Nonionic Surfactants Generally

Nonionic surfactants are compounds well known in themselves (see, e.g., in this regard, "Handbook of Surfactants" by M. R. Porter, Blackie & Son publishers (Glasgow and London), 1991, pp. 116-178), which is incorporated herein by reference in its entirety.

The nonionic surfactant can be, for example, selected from alcohols, alpha-diols, alkylphenols and esters of fatty acids, these compounds being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and a mixture thereof.

The nonionic surfactants may preferably be chosen from polyoxyalkylenated or polyglycerolated nonionic surfactants. The oxyalkylene units are more particularly oxyethylene or oxypropylene units, or a combination thereof, and are preferably oxyethylene units.

Examples of oxyalkylenated nonionic surfactants that may be mentioned include: oxyalkylenated ($C_8$-$C_{24}$)alkylphenols, saturated or unsaturated, linear or branched, oxyalkylenated $C_8$-$C_{30}$ alcohols, saturated or unsaturated, linear or branched, oxyalkylenated $C_8$-$C_{30}$ amides, esters of saturated or unsaturated, linear or branched, $C_8$-$C_{30}$ acids and of polyethylene glycols, polyoxyalkylenated esters of saturated or unsaturated, linear or branched, $C_8$-$C_{30}$ acids and of sorbitol, saturated or unsaturated, oxyalkylenated plant oils, condensates of ethylene oxide and/or of propylene oxide, inter alia, alone or as mixtures.

The surfactants preferably contain a number of moles of ethylene oxide and/or of propylene oxide of between 2 and 100 and most preferably between 2 and 50.

In accordance with one preferred embodiment of the invention, the oxyalkylenated nonionic surfactants are chosen from oxyethylenated $C_8$-$C_{30}$ alcohols.

Examples of ethoxylated fatty alcohols (or $C_8$-$C_{30}$ alcohols) that may be mentioned include the adducts of ethylene oxide with lauryl alcohol, especially those containing from 9 to 50 oxyethylene groups and more particularly those containing from 10 to 25 oxyethylene groups (Laureth-10 to Laureth-25); the adducts of ethylene oxide with behenyl alcohol, especially those containing from 9 to 50 oxyethylene groups (Beheneth-9 to Beheneth-50); the adducts of ethylene oxide with cetearyl alcohol (mixture of cetyl alcohol and stearyl alcohol), especially those containing from 10 to 30 oxyethylene groups (Ceteareth-10 to Ceteareth-30); the adducts of ethylene oxide with cetyl alcohol, especially those containing from 10 to 30 oxyethylene groups (Ceteth-10 to Ceteth-30); the adducts of ethylene oxide with stearyl alcohol, especially those containing from 10 to 30 oxyethylene groups (Steareth-10 to Steareth-30); the adducts of ethylene oxide with isostearyl alcohol, especially those containing from 10 to 50 oxyethylene groups (Isosteareth-10 to Isosteareth-50); and a mixture thereof.

As examples of polyglycerolated nonionic surfactants, polyglycerolated $C_8$-$C_{40}$ alcohols are preferably used.

In particular, the polyglycerolated $C_8$-$C_{40}$ alcohols correspond to the following formula:

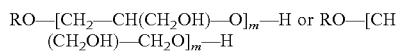

in which R represents a linear or branched $C_8$-$C_{40}$ and preferably $C_8$-$C_{30}$ alkyl or alkenyl radical, and m represents a number ranging from 1 to 30 and preferably from 1.5 to 10.

As examples of compounds that are suitable in the context of the invention, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

According to one of the embodiments according to the present invention, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and a mixture thereof.

Examples of ethoxylated fatty esters that may be mentioned include the adducts of ethylene oxide with esters of lauric acid, palmitic acid, stearic acid or behenic acid, and a mixture thereof, especially those containing from 9 to 100 oxyethylene groups, such as PEG-9 to PEG-50 laurate; PEG-9 to PEG-50 palmitate; PEG-9 to PEG-50 stearate; PEG-9 to PEG-50 palmitostearate; PEG-9 to PEG-50 behenate; polyethylene glycol 100 EO monostearate; and a mixture thereof.

As glyceryl esters of fatty acids, glyceryl stearate (glyceryl mono-, di- and/or tristearate) (glyceryl stearate) or glyceryl ricinoleate and a mixture thereof can in particular be cited.

As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be cited.

Mixtures of these surfactants, such as for example the product containing glyceryl stearate and PEG-100 stearate, marketed under the name ARLACEL 165 by Croda, and a product containing glyceryl stearate (glyceryl mono- and distearate) and potassium stearate, can also be used.

The sorbitol esters of $C_8$-$C_{24}$ fatty acids and alkoxylated derivatives thereof can be selected from sorbitan palmitate, sorbitan trioleate and esters of fatty acids and alkoxylated sorbitan containing for example from 20 to 100 EO, such as for example polyethylene sorbitan trioleate (polysorbate 85) or the compounds marketed under the trade names Tween 20 or Tween 60 by Croda.

As esters of fatty acids and glucose or alkylglucose, in particular glucose palmitate, alkylglucose sesquistearates such as methylglucose sesquistearate, alkylglucose palmitates such as methylglucose or ethylglucose palmitate, methylglucoside fatty esters and more specifically the diester of methylglucoside and oleic acid (Methyl glucose dioleate), the mixed ester of methylglucoside and the mixture oleic acid/hydroxystearic acid (Methyl glucose dioleate/hydroxystearate), the ester of methylglucoside and isostearic acid (Methyl glucose isostearate), the ester of methylglucoside and lauric acid (Methyl glucose laurate), the mixture of monoester and diester of methylglucoside and isostearic acid (Methyl glucose sesqui-isostearate), the mixture of monoester and diester of methylglucoside and stearic acid (Methyl glucose sesquistearate) and in particular the product marketed under the name Glucate SS by Lubrizol, and a mixture thereof can be cited.

As ethoxylated ethers of fatty acids and glucose or alkylglucose, ethoxylated ethers of fatty acids and methylglucose, and in particular the polyethylene glycol ether of the diester of methylglucose and stearic acid with about 20 moles of ethylene oxide (PEG-20 methyl glucose distearate) such as the product marketed under the name GLUCAM E-20 DISTEARATE by Lubrizol, the polyethylene glycol ether of the mixture of monoester and diester of methylglucose and stearic acid with about 20 moles of ethylene oxide (PEG-20 methyl glucose sesquistearate) and in particular the product marketed under the name GLUCAMATE SSE-20 by Lubrizol, and a mixture thereof, can for example be cited.

As sucrose esters, saccharose palmito-stearate, saccharose stearate and saccharose monolaurate can for example be cited.

As sugar ethers, alkylpolyglucosides can be used, and for example decylglucoside such as the product marketed under the name MYDOL 10 by Kao Chemicals, the product marketed under the name PLATAREN 2000 by BASF, and the product marketed under the name ORAMIX NS 10 by Seppic, caprylyl/capryl glucoside such as the product marketed under the name ORAMIX CG 110 by Seppic or under the name LUTENSOL GD 70 by BASF, laurylglucoside such as the products marketed under the names PLANTAREN 1200 N and PLANTACARE 1200 by BASF, cocoglucoside such as the product marketed under the name PLANTACARE 818/UP by BASF, cetostearyl glucoside possibly mixed with cetostearyl alcohol, marketed for example under the name MONTANOV 68 by Seppic, under the name TEGO-CARE CG90 by Evonik, arachidyl glucoside, for example in the form of the mixture of arachidyl and behenyl alcohols and arachidyl glucoside marketed under the name MONTANOV 202 by Seppic, cocoylethylglucoside, for example in the form of the mixture (35/65) with cetyl and stearyl alcohols, marketed under the name MONTANOV 82 by Seppic, and a mixture thereof can in particular be cited.

Mixtures of glycerides of alkoxylated plant oils such as mixtures of ethoxylated (200 EO) palm and copra (7 EO) glycerides can also be cited.

The nonionic surfactant may be selected from the group consisting of PEG-7 glyceryl cocoate, PEG-20 methylglucoside sesquistearate, PEG-20 glyceryl tri-isostearate, PG-5 dioleate, PG-4 diisostearate, PG-10 isostearate, PEG-8 isostearate, and PEG-60 hydrogenated castor oil.

Mixtures of these oxyethylenated derivatives of fatty alcohols and of fatty esters may also be used.

In some case, the nonionic surfactant is a fatty alkanolamide. Non-limiting examples of fatty alkanolamides that may be used include cocamide MEA, cocamide DEA, soyamide DEA, lauramide DEA, oleamide MIPA, stearamide MEA, myristamide DEA, stearamide DEA, oleylamide DEA, tallowamide DEA lauramide MIPA, tallowamide MEA, isostearamide DEA, isostearamide MEA, and a mixture thereof.

Cationic Conditioning Polymers

In various embodiments, the hair coloring compositions of the instant disclosure include one or more cationic conditioning polymers. However, in other embodiments, the hair coloring compositions are free or essentially free from cationic conditioning polymer.

Non-limiting examples of cationic polymers include copolymers of 1-vinyl-2-pyrrolidine and 1-vinyl-3-methylimidazolium salt (e.g., chloride salt) (referred to as Polyquaternium-16); copolymers of 1-vinyl-2-pyrrolidine and dimethylaminoethyl methacrylate (referred to as Polyquaternium-11); cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7); polysaccharide polymers, such as cationic cellulose derivatives and cationic starch derivatives. Cationic cellulose is available as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). Additionally, or alternatively, the cationic conditioning polymers may include or be chosen from cationic guar gum derivatives, such as guar hydroxypropyltrimonium chloride.

In certain embodiments, the one or more cationic conditioning polymers include cationic polysaccharide polymers, such as cationic cellulose, cationic starch, and cationic guar gum. In the context of the instant disclosure cationic polysaccharide polymers include cationic polysaccharides and polysaccharide derivatives (e.g., derivatized to be cationic), for example, resulting in cationic cellulose (cellulose derivatized to be cationic), cationic starch (derivatized to be cationic), cationic guar (guar derivatized to be cationic).

Non-limiting examples of cationic celluloses include hydroxyethylcellulose (also known as HEC), hydroxymethylcellulose, methylhydroxyethylcellulose, hydroxypropylcellulose (also known as HPC), hydroxybutylcellulose, hydroxyethylmethylcellulose (also known as methyl hydroxyethylcellulose) and hydroxypropylmethylcellulose (also known as HPMC), cetyl hydroxyethylcellulose, polyquaternium-10, polyquaternium-24, and mixtures thereof, preferably polyquaternium-10, polyquaternium-24, and mixtures thereof.

Non-limiting examples of cationic guar include guar hydroxypropyltrimonium chloride, hydroxypropyl guar hydroxypropyltrimonium chloride, Non-limiting examples of cationic starch include starch hHydroxypropyltrimonium chloride, hydroxypropyl oxidized starch PG trimonium chloride, and a mixture thereof.

In various embodiments, the one or more cationic conditioning polymers are chosen from polyquaterniums. Non-limiting examples include Polyquaternium-1 (ethanol, 2,2', 2"-nitrilotris-, polymer with 1,4-dichloro-2-butene and N,N, N',N'-tetramethyl-2-butene-1,4-diamine), Polyquaternium- 2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), Polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), Polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/ diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (quaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), Polyquaternium-47 (terpolymer of acrylic acid, methacrylamidopropyl trimethylammonium chloride, and methyl acrylate), and/or Polyquaternium-67.

In various embodiments, the one or more cationic conditioning polymers are chosen from cationic cellulose derivatives, quaternized hydroxyethyl cellulose (e.g., polyquaternium-10), cationic starch derivatives, cationic guar gum derivatives, copolymers of acrylamide and dimethyldiallyammonium chloride (e.g., polyquaternium-7), polyquaterniums, and a mixture thereof. For example, the cationic polymer(s) may be selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, polyquaternium-67 and a mixture thereof. A combination of two or more polyquaterniums can be useful. A particularly preferred and useful cationic polymer is polyquaternium-10.

The cationic polymers may be a polyquaternium. In certain embodiments, the cationic surfactants may be polyquaterniums selected from polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof.

In some embodiments, the one or more cationic conditioning polymers are chosen from cationic proteins and cationic protein hydrolysates (e.g., hydroxypropyltrimonium hydrolyzed wheat protein), quaternary diammonium polymers (e.g., hexadimethrine chloride), copolymers of acrylamide and dimethyldiallyammonium chloride, and mixtures thereof.

The cationic conditioning polymers may be homopolymers or formed from two or more types of monomers. The molecular weight of the polymer may be between 5,000 and 10,000,000, typically at least 10,000, and preferably in the range 100,000 to about 2,000,000. These polymers will typically have cationic nitrogen containing groups such as quaternary ammonium or protonated amino groups, or a mixture thereof.

The cationic charge density is suitably at least 0.1 meq/g, preferably above 0.8 or higher. In some instances, the cationic charge density does not exceed 3 meq/g, or does not exceed 2 meq/g. The charge density can be measured using the Kjeldahl method and can be within the above limits at the desired pH of use, which will in general be from about 3 to 9 and preferably between 4 and 8.

The cationic nitrogen-containing group will generally be present as a substituent on a fraction of the total monomer units of the cationic conditioning polymer. Thus when the polymer is not a homopolymer it can contain spacer non-cationic monomer units.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$-$C_7$ alkyl groups, more preferably $C_1$-$C_3$ alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition.

Amine substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$-$C_3$ alkyls, more preferably $C_1$ and $C_2$ alkyls.

Suitable amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$, alkyls.

The cationic conditioning polymers can comprise mixtures of monomer units derived from amine- and/or quaternary ammonium-substituted monomer and/or compatible spacer monomers.

Suitable cationic conditioning polymers include, for example: copolymers of 1-vinyl-2-pyrrolidine and 1-vinyl-3-methyl-imidazolium salt (e.g., Chloride salt) (referred to as Polyquaternium-16) such as those commercially available from BASF under the LUVIQUAT tradename (e.g., LUVIQUAT FC 370); copolymers of 1-vinyl-2-pyrrolidine and dimethylaminoethyl methacrylate (referred to as Polyquaternium-11) such as those commercially from Gar Corporation (Wayne, N.J., USA) under the GAFQUAT tradename (e.g., GAFQUAT 755N); and cationic diallyl quaternary ammonium-containing polymer including, for example, dimethyldiallyammonium chloride homopolymer and copolymers of acrylamide and dimethyldiallyammonium chloride (referred to as Polyquaternium-6 and Polyquaternium-7).

Other cationic conditioning polymers that can be used include polysaccharide polymers, such as cationic cellulose derivatives and cationic starch derivatives. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide (referred to as Polyquaternium-10). Another type of cationic cellulose includes the polymeric quaternary ammonium salts of hydroxyethyl cellulose reacted with lauryl dimethyl ammonium-substituted epoxide (referred to as Polyquaternium-24). These materials are available from Amerchol Corp. (Edison, N.J., USA) under the tradename Polymer LM-200.

Other cationic conditioning polymers that can be used include cationic guar gum derivatives, such as guar hydroxypropyltrimonium chloride.

Polyquaterniums include Polyquaternium-1 (ethanol, 2,2', 2''-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (quaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylen oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quaternized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), and Polyquaternium-47 (terpolymer of acrylic acid, methacrylamidopropyl trimethylammonium chloride, and methyl acrylate).

If present the total amount of the one or more cationic conditioning polymers will vary. Nonetheless, in various embodiments, the total amount of the one or more cationic conditioning polymer is from about 0.01 to about 6 wt. %, based on the total weight of the hair coloring composition. In further embodiments, the total amount of the one or more cationic conditioning polymers is from about 0.01 to about 5 wt. %, about 0.01 to about 3 wt. %, about 0.05 to about 6 wt. %, about 0.05 to about 3 wt. %, about 0.1 to about 6 wt. %, about 0.1 to about 5 wt. %, about 0.1 to about 3 wt. %, based on the total weight of the hair coloring composition.

Thickening Agents

In various embodiments, the hair coloring compositions of the instant disclosure include one or more thickening agents. However, in other embodiments, the hair coloring compositions are free or essentially free from thickening agents.

Nonlimiting examples of thickening agents include:

a. Carboxylic acid or carboxylate based homopolymer or co-polymer, which can be linear or crosslinked: These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickeners useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

b. Celluloses: Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC).

c. Polyvinylpyrrolidone (PVP) and co-polymers: Nonlimiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commerically available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

d. Sucrose esters: Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

e. Polyglyceryl esters: Non-limiting polyglycerol esters of fatty acids (polygylceryl esters) include those of the following formula:

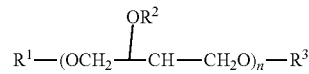

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, nonlimiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

f. C8-24 hydroxyl substituted aliphatic acid and C8-24 conjugated aliphatic acid: Non-limiting examples include conjugated linoleic acid, cis-parinaric acid, trans-7-octadecenoic acid, cis-5,8,11,14,17-eicosapentanoic acid, cis-4,7,10,13,16,19-docosahexenoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, cis-11,14,17-eicosatrienoic acid, cis-5-eicosenoic acid, cis-8,11,14-eicosatrienoic acid, hexadecatrienoic acid, palmitoleic acid, petroselaidic acid, trans trans farnesol, cis-13,16-docosadienoic acid, cis-vaccenic acid, cis-11-eicosenoic acid, cis-13,16,19-docosatrienoic acid, cis-13-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, pinolenic acid, trans-13-octadecenoic acid. More preferably, the aliphatic acid comprises 12-hydroxystearic acid, conjugated linoleic acid, or a mixture thereof.

g. Gums: Non-limiting examples of gums include gum arabic, tragacanth gum, karaya gum, guar gum, gellan gum, tara gum, locust bean gum, tamarind gum, xanthan gum, locust bean gum, Seneca gum, sclerotium gum, gellan gum, etc.

If present, the total amount of thickening polymers in the hair coloring compositions will vary. Nonetheless, in various embodiments, the total amount of the one or more thickening agents in the hair coloring composition is from about 0.01 to about 6 wt. %, based on the total weight of the hair coloring composition. In further embodiments, the total amount of the one or more thickening agents is from about 0.01 to about 5 wt. %, about 0.01 to about 3 wt. %, about 0.05 to about 6 wt. %, about 0.05 to about 3 wt. %, about 0.1 to about 6 wt. %, about 0.1 to about 5 wt. %, about 0.1 to about 3 wt. %, based on the total weight of the hair coloring composition.

pH

The pH of the hair coloring composition will vary. Nonetheless, in various embodiments, the pH of the hair coloring compositions is from about 2 to about 9. In further embodiments, the pH of the compositions is from about 2 to about 8, about 2 to about 7, about 2 to about 6, about 2 to about 5, about 3 to about 9, about 3 to about 8, about 3 to about 7, about 3 to about 6, about 3 to about 5, about 3.5 to about 9, about 3.5 to about 8, about 3.5 to about 7, about 3.5 to about 6, about 3.5 to about 5, about 4 to about 9, about 4 to about 8, about 4 to about 7, about 4 to about 6, or about 4 to about 5.

Viscosity

The viscosity of the hair coloring composition will vary. In various embodiments, the viscosity of the composition is from about 1 to about 25,000 cps at 25° C. using a #4 spindle at 100 rpm using a Rheomat RM 180 or similar device. In some cases, the viscosity of the composition may be about 1 to about 20,000 cps, about 1 to about 15,000 cps, about 1 to about 10,000 cps, about 1 to about 5,000 cps, about 1 to about 1,000 cps, about 10 to about 20,000 cps, about 10 to about 15,000 cps, about 10 to about 10,000 cps, about 10 to about 5,000 cps, or about 10 to about 1,000 cps. In various embodiments, the viscosity of the composition is water-like and is easily sprayed through a hand-pump spray nozzle to form a mist.

Methods

The hair coloring compositions of the instant disclosure are useful in methods for coloring hair. The methods include applying a hair coloring composition according to the instant disclosure to the hair. The hair coloring compositions may be applied to dry hair, wet hair, or damp hair. The methods do not require a "processing" step or amount of time for activation and deposition for the color to develop. The hair coloring compositions can be applied to the hair and allowed to remain on the hair for an indefinite amount of time. For example, after applying the hair coloring composition to the hair, the hair can be styled without first rinsing the hair coloring composition from the hair.

In various embodiments, the hair coloring composition is applied to the hair and allowed to remain on the hair for a period of time, and then rinsed or shampooed from the hair. For example, the hair coloring composition may be applied to the hair and the hair coloring composition allowed to remain on the hair for 5, 10, 15, 20, 30, or 45 minutes before rinsing or shampooing the hair coloring composition from the hair. In certain embodiments, the hair coloring composition is applied to the hair and allowed to dry on the hair (the hair containing the hair coloring composition is dried). After drying the hair can optionally be rinsed or shampooed, and optionally styled.

The hair coloring compositions can be applied to the hair by any method known in the art. In various embodiments, the hair coloring compositions are sprayed onto the hair. After initial application of the hair coloring compositions to the hair, it is often preferable to massage or comb in the hair coloring compositions into and throughout the hair so that the hair coloring compositions reach the entirety of the hair to be colored.

EMBODIMENTS

In various embodiments, the hair coloring composition comprises or consists of:
(a) about 1 to about 25 wt. %, preferably about 2 to about 20, more preferably about 5 to about 15 wt. % of aloe barbadensis leaf juice;
(b) about 1 to about 10 wt. %, preferably about 1 to about 8 wt. %, more preferably about 2 to about 6 wt. % of one or more polyether-modified polysiloxanes;
(c) about 0.5 to about 10 wt. %, preferably about 1 to about 6 wt. %, more preferably about 1.5 to about 5 wt. % of one or more non-silicone nonionic surfactants selected from alkoxylated compounds;
(d) about 0.05 to about 8 wt. %, more preferably about 0.1 to about 6 wt. %, more preferably about 0.1 to about 4 wt. % of one or more cationic surfactants;
(e) optionally, one or more water-soluble organic solvents;
(f) one or more direct dyes; and
(g) about 60 to about 92 wt. %, more preferably about 70 to about 90 wt. %, more preferably about 75 to about 90 wt. % of water;
 wherein all weight percentages are based on the total weight of the hair coloring composition.

In various embodiments, the one or more polyether-modified polysiloxanes are selected PEG/PPG-18/18 dimethicone, PEG-12 dimethicone, PEG-14 dimethicone, siloxane polyalkyleneoxide copolymer, PEG/PPG-22/24 dimethicone, PEG/PPG-17/18 dimethicone, PEG/PPG-20/6 dimethicone, PEG/PPG-14/4 dimethicone, and mixtures thereof, preferably chosen from PEG-12 dimethicone, PEG-14 dimethicone, and a mixture thereof.

In various embodiments, the one or more non-silicone nonionic surfactants selected from alkoxylated compounds are chosen from straight chain primary alcohol alkoxylates, straight chain secondary alcohol alkoxylates, alkyl phenol alkoxylates, olefinic alkoxylates, branched chain alkoxylates, fatty oil or hydrogenated fatty oil ethoxylates, alkyl sorbitan esters ethoxylates, alkyl glyceride ethoxylates, and mixtures thereof.

In various embodiment, at least one of the one or more cationic surfactants is selected from dialkyl dimonium halide compounds. In further embodiments, the at least one dialkyl dimonium halide compound is selected from di-C12-15 alkyl dimonium chloride, C12-18 dialkyldimonium chloride, di-C12-18 alkyl dimonium chloride, dicapryl/dicaprylyl dimonium chloride, didecyldimonium chloride, dicetyldimonium chloride, ditallowdimonium chloride, dicocodimonium chloride, distearyldimonium chloride, ceteardimonium chloride, hydroxyethyl oleyl dimonium chloride, panthenyl hydroxypropyl steardimonium chloride, hydroxypropyl bis-hydroxyethyldimonium chloride, hydroxypropyl bisstearyldimonium chloride, hydroxycetyl hydroxyethyl dimonium chloride, hydroxyethyl behenamidopropyl dimonium chloride, behenamidopropyl PG-dimonium chloride, cocamidopropyl PG-dimonium chloride, oleamidopropyl PG-dimonium chloride, behentrimonium chloride, and mixtures thereof.

In various embodiments, the one or more water-soluble organic solvents are chosen from glycerin, mono-alcohols, polyols (polyhydric alcohols), glycols, and a mixture thereof.

In various embodiments, the one or more direct dyes are chosen from nitro-phenylenediamines, nitro-aminophenols, azo dyes, anthraquinones, triarylmethane dyes, indophenols, and a combination thereof.

In various embodiments, the hair coloring composition has a viscosity appropriate for it to be applied as a spray. In further embodiments, the hair coloring composition is a spray.

In various embodiments, the hair coloring composition is free or essentially free from amino silicones, for example, amodimethicone In various embodiments, the hair coloring composition is free or essentially free from parabens.

In various embodiments, the hair coloring composition is free or essentially free from polyorganosiloxanes other than the polyether-modified polysiloxanes of (c).

In various embodiments, the hair coloring composition is free or essentially free from oxidative dye precursors.

In various embodiments, the hair coloring composition is free or essentially free from film forming polymers.

In various embodiments, the hair coloring composition is free or essentially free from thickening polymers.

In various embodiments, the hair coloring composition comprises one or more miscellaneous components (also referred to as "miscellaneous ingredients"). In certain embodiments, the hair coloring compositions includes from about 0.1 to about 10 wt. %, preferably about 0.1 to about 6 wt. %, more preferably about 0.5 to about 5 wt. % of one or more miscellaneous components, based on the total weight of the hair treatment composition. In a preferred embodiment, the one or more miscellaneous components are selected from antioxidants, pH adjusters, salts, fragrances, preservatives, botanical extracts, chelating agents, vitamins, amino acids, cosmetic colorants, and mixtures thereof.

In various embodiments, the hair coloring composition comprises or consists of:
(a) about 1 to about 25 wt. %, preferably about 2 to about 20, more preferably about 5 to about 15 wt. % of aloe barbadensis leaf juice;
(b) about 1 to about 10 wt. %, preferably about 1 to about 8 wt. %, more preferably about 2 to about 6 wt. % of one or more polyether-modified polysiloxanes selected from PEG/PPG-18/18 dimethicone, PEG-12 dimethicone, PEG-14 dimethicone, siloxane polyalkyleneoxide copolymer, PEG/PPG-22/24 dimethicone, PEG/PPG-17/18 dimethicone, PEG/PPG-20/6 dimethicone, PEG/PPG-14/4 dimethicone, and mixtures thereof, preferably chosen from PEG-12 dimethicone, PEG-14 dimethicone, and a mixture thereof, even more preferably PEG-12 dimethicone;
(c) about 0.5 to about 10 wt. %, preferably about 1 to about 6 wt. %, more preferably about 1.5 to about 5 wt. % of one or more non-silicone nonionic surfactants selected from straight chain primary alcohol alkoxylates, straight chain secondary alcohol alkoxylates, alkyl phenol alkoxylates, olefinic alkoxylates, branched chain alkoxylates, fatty oil or hydrogenated fatty oil ethoxylates, alkyl sorbitan esters ethoxylates, alkyl glyceride ethoxylates, and mixtures thereof, preferably selected from fatty oil or hydrogenated fatty oil ethoxylates, for example, PEG-40 hydrogenated castor oil;
(d) about 0.05 to about 8 wt. %, more preferably about 0.1 to about 6 wt. %, more preferably about 0.1 to about 4 wt. % of one or more cationic surfactants selected from dialkyl dimonium halide compounds;
(e) about 0.05 to about 15 wt. %, preferably about 0.1 to about 10 wt. %, more preferably about 0.5 to about 5 wt. % of one or more water-soluble organic solvents selected from glycerin, mono-alcohols, polyols (polyhydric alcohols), glycols, and a mixture thereof, more preferably selected from glycerin and glycols;
(f) one or more direct dyes, preferably one or more cationic direct dyes;
(g) about 60 to about 92 wt. %, more preferably about 70 to about 90 wt. %, more preferably about 75 to about 90 wt. % of water;
(h) about 0.1 to about 10 wt. %, preferably about 0.1 to about 6 wt. %, more preferably about 0.5 to about 5 wt. % of one or more miscellaneous components selected from antioxidants, pH adjusters, salts, fragrances, preservatives, botanical extracts, chelating agents, vitamins, amino acids, cosmetic colorants, and mixtures thereof; and
(i) optionally, one or more cationic conditioning polymers and/or one or more thickening agents, for example, in an amount from about 0.01 to about 5 wt. %, preferably from about 0.05 to about 4 wt. %, more preferably from about 0.1 to about 3 wt. %;
wherein all weight percentages are based on the total weight of the hair coloring composition.

In further embodiments, the hair coloring composition comprises or consists of:
(a) about 1 to about 25 wt. %, preferably about 2 to about 20, more preferably about 5 to about 15 wt. % of aloe barbadensis leaf juice;
(b) about 1 to about 10 wt. %, preferably about 1 to about 8 wt. %, more preferably about 2 to about 6 wt. % of one or more polyether-modified polysiloxanes selected from selected from PEG/PPG-18/18 dimethicone, PEG-12 dimethicone, PEG-14 dimethicone, siloxane polyalkyleneoxide copolymer, PEG/PPG-22/24 dimethicone, PEG/PPG-17/18 dimethicone, PEG/PPG-20/6 dimethicone, PEG/PPG-14/4 dimethicone, and mixtures thereof, preferably chosen from PEG-12 dimethicone, PEG-14 dimethicone, and a mixture thereof, even more preferably PEG-12 dimethicone;

(c) about 0.5 to about 10 wt. %, preferably about 1 to about 6 wt. %, more preferably about 1.5 to about 5 wt. % of one or more non-silicone nonionic surfactants selected from straight chain primary alcohol alkoxylates, straight chain secondary alcohol alkoxylates, alkyl phenol alkoxylates, olefinic alkoxylates, branched chain alkoxylates, fatty oil or hydrogenated fatty oil ethoxylates, alkyl sorbitan esters ethoxylates, alkyl glyceride ethoxylates, and mixtures thereof, preferably selected from fatty oil or hydrogenated fatty oil ethoxylates, for example, PEG-40 hydrogenated castor oil;

(d) about 0.05 to about 8 wt. %, more preferably about 0.1 to about 6 wt. %, more preferably about 0.1 to about 4 wt. % of one or more cationic surfactants selected from dialkyl dimonium halide compounds, preferably chosen from di-C12-15 alkyl dimonium chloride, C12-18 dialkyldimonium chloride, di-C12-18 alkyl dimonium chloride, dicapryl/dicaprylyl dimonium chloride, didecyldimonium chloride, dicetyldimonium chloride, ditallowdimonium chloride, dicocodimonium chloride, distearyldimonium chloride, ceteardimonium chloride, hydroxyethyl oleyl dimonium chloride, panthenyl hydroxypropyl steardimonium chloride, hydroxypropyl bis-hydroxyethyldimonium chloride, hydroxypropyl bisstearyldimonium chloride, hydroxycetyl hydroxyethyl dimonium chloride, hydroxyethyl behenamidopropyl dimonium chloride, behenamidopropyl PG-dimonium chloride, cocamidopropyl PG-dimonium chloride, oleamidopropyl PG-dimonium chloride, behentrimonium chloride, and mixtures thereof, more preferably hydroxyethyl oleyl dimonium chloride;

(e) about 0.05 to about 15 wt. %, preferably about 0.1 to about 10 wt. %, more preferably about 0.5 to about 5 wt. % of one or more water-soluble organic solvents selected from glycerin, mono-alcohols, polyols (polyhydric alcohols), glycols, and a mixture thereof, preferably selected from glycerin and glycols, for example, propylene glycol;

(f) one or more direct dyes, preferably one or more cationic direct dyes;

(g) about 60 to about 92 wt. %, more preferably about 70 to about 90 wt. %, more preferably about 75 to about 90 wt. % of water; and (h) about 0.1 to about 10 wt. %, preferably about 0.1 to about 6 wt. %, more preferably about 0.5 to about 5 wt. % of one or more miscellaneous components selected from antioxidants, pH adjusters, salts, fragrances, preservatives, botanical extracts, chelating agents, vitamins, amino acids, cosmetic colorants, and mixtures thereof;

wherein all weight percentages are based on the total weight of the hair coloring composition.

In various embodiments, the hair coloring compositions are homogenous single-phase liquid.

The pH of the hair coloring compositions in the embodiments above are as disclosed throughout the disclosure. For example, in various embodiments, the pH of the hair coloring compositions is from about 2 to about 9. In further embodiments, the pH of the compositions is from about 2 to about 8, about 2 to about 7, about 2 to about 6, about 2 to about 5, about 3 to about 9, about 3 to about 8, about 3 to about 7, about 3 to about 6, about 3 to about 5, about 3.5 to about 9, about 3.5 to about 8, about 3.5 to about 7, about 3.5 to about 6, about 3.5 to about 5, about 4 to about 9, about 4 to about 8, about 4 to about 7, about 4 to about 6, or about 4 to about 5.

The viscosity of the hair coloring compositions in the embodiments above are as disclosed throughout the disclosure. For example, the viscosity of the composition is from about 250 to about 2000 cps at 25° C. using a #4 spindle at 100 rpm. In some cases, the viscosity of the composition may be about 500 to about 2500 cps, about 500 to about 2000 cps, about 500 to about 1500 cps, about 600 to about 1300 cps, or about 650 to about 1200 cps at 25° C. using a #4 spindle at 100 rpm. measured at 25° C. using a M3 spindle at 100 rpm, for example, using a Rheomat RM 180.

EXAMPLES

Implementation of the present disclosure is provided by way of the following examples. The examples serve to illustrate the technology without being limiting in nature.

Example 1

|     |     |     | Inventive | | | | Comparative | | | | |
| --- | --- | --- | --- | --- | --- | --- | --- | --- | --- | --- | --- |
|     |     |     | A | B | C | D | C1 | C2 | C3 | C4 | C5 |
| (a) | Aloe Barbadensis Leaf Juice | | 10 | 10 | 10 | 10 | | | | | |
|     | Amino Silicone | AMODIMETHICONE | | | | | 10 | 5 | 2.5 | 1 | 0.25 |
| (b) | polyether-modified polysiloxane | PEG-14 DIMETHICONE | 2.8 | 2.8 | 2.8 | 2.8 | 2.8 | 2.8 | 2.8 | 2.8 | 2.8 |
| (c) | Nonionic Surfactant | PEG-40 HYDROGENATED CASTOR OIL | 1.6 | 1.6 | 1.6 | 1.6 | 1.6 | 1.6 | 1.6 | 1.6 | 1.6 |
| (d) | Cationic Surfactant | HYDROXYETHYL OLEYL DIMONIUM CHLORIDE | 0.2 | 0.2 | 0.2 | 0.2 | 0.2 | 0.2 | 0.2 | 0.2 | 0.2 |
| (e) | WS Organic Solvent | PROPYLENE GLYCOL | 1.2 | 1.2 | 1.2 | 1.2 | 1.2 | 1.2 | 1.2 | 1.2 | 1.2 |
| (f) | Direct Dyes 0.001-2 wt. % | BASIC YELLOW 87, BASIC YELLOW 57, BASIC BROWN 17, HC BLUE NO. 15, BASIC ORANGE 31, BASIC RED 51 HC BLUE NO. 2, 2-NITRO-5-GLYCERYL METHYLANILINE, Etc. | Natural Brown | Auburn | Copper | Vivid Red | Vivid Red | Vivid Red | Vivid Red | Vivid Red | Vivid Red |

-continued

|     |       |                                                                  | Inventive |     |     |     | Comparative |     |     |     |     |
|-----|-------|------------------------------------------------------------------|-----------|-----|-----|-----|-------------|-----|-----|-----|-----|
|     |       |                                                                  | A         | B   | C   | D   | C1          | C2  | C3  | C4  | C5  |
| (h) | Misc. | Antioxidants, pH Adjusters, Salts, Fragrances, Preservatives, Etc.[1] | ≤3        | ≤3  | ≤3  | ≤3  | ≤3          | ≤3  | ≤3  | ≤3  | ≤3  |
| (g) |       | WATER                                                            | qs        | qs  | qs  | qs  | qs          | qs  | qs  | qs  | qs  |
|     |       | pH (+/−0.3)                                                      | 4.5       | 4.5 | 4.5 | 4.5 | 4.5         | 4.5 | 4.5 | 4.5 | 4.5 |
|     |       | Stable                                                           | Y         | Y   | Y   | Y   | N           | N   | N   | N   | N   |

[1]PENTAERYTHRITYL TETRA-DI-T-BUTYL, HYDROXYHYDROCINNAMATE, CITRIC ACID, SODIUM CHLORIDE, FRAGRANCE, POTASSIUM SORBATE, SODIUM BENZOATE, PHENOXYETHANOL, AND/OR VEGETAL EXTRACTS, ETC.

Example 2

Stability Study

The compositions of Example 1 were prepared, and the stability of the compositions visually assessed. Amodimethicone is a synthetic material but is commonly used in hair treatment products, especially conditioning products. It is used for its smoothing, anti-frizz, and light-weight characteristics. Amodimethicone however, caused stability problems when incorporated into compositions similar to those of the instant case, even when used in very low amounts. Comparative Compositions F-J included varying amounts of amodimethicone, i.e., 10, 5, 2.5, 1, and 0.25 wt. % of amodimethicone. Comparative Composition F is identical to Inventive Composition D except that amodimethicone in an amount of 10 wt % of used instead of aloe barbadensis leaf juice in an amount of 10 wt. % Comparative Compositions G-J were identical to Inventive Composition F except that consecutively lower amounts of amodimethicone were included. The reduced amount of amodimethicone was replaced with additional water. The stability for all composition was assessed after 24 hours. All compositions were prepared and allow to sit for 24 hours at room temperature (about 25° C.). All compositions containing amodimethicone, regardless of the amount, phase separated. The amodimethicone separated from the water and formed a layer above the water.

The inventors discovered that aloe barbadensis leaf juice can be incorporated into the compositions without destabilizing the compositions, at high amount (10 wt. %). The inventive compositions in Example 1 include 10 wt. % of aloe barbadensis leaf juice because this is the highest amount of amodimethicone tested. Unlike amodimethicone, aloe barbadensis leaf juice is natural. Yet it provides significant conditioning properties to hair, for example, smoothing, anti-frizz, and light-weight characteristics.

Example 3

Wash Study

Inventive Composition D from Example 1 is included in the table below, which includes a combination of direct dyes providing a vivid red color to hair. Comparative Composition C6 includes the same direct dyes in the same amount as Inventive Composition D in only deionized water. Thus, Comparative Composition C6 functions as a type of control.

Comparative Compositions C7-C9 are identical to Inventive Composition D except that PEG-14 dimethicone was omitted from Comparative Composition C7, Aloe Baradensis leaf juice was omitted from Comparative Composition C8, and hydroxyethyl olely dimonium chloride was omitted from Comparative Composition C9.

|     |                               |                                                         | Inventive | Comparative |     |     |     |
|-----|-------------------------------|---------------------------------------------------------|-----------|-------------|-----|-----|-----|
|     |                               |                                                         | D         | C6          | C7  | C8  | C9  |
| (a) |                               | ALOE BARBADENSIS LEAF JUICE                             | 10        |             | 10  |     | 10  |
| (b) | polyether-modified polysiloxane | PEG-14 DIMETHICONE                                    | 2.8       |             |     | 2.8 | 2.8 |
| (c) | Nonionic Surfactant           | PEG-40 HYDROGENATED CASTOR OIL                          | 1.6       |             | 1.6 | 1.6 | 1.6 |
| (d) | Cationic Surfactant           | HYDROXYETHYL OLEYL DIMONIUM CHLORIDE                    | 0.2       |             | 0.2 | 0.2 |     |
| (e) | WS Organic Solvent            | PROPYLENE GLYCOL                                        | 1.2       |             | 1.2 | 1.2 | 1.2 |
| (f) | Direct Dye                    | Vivid Red                                               |           | 0.001-2 wt. % |   |     |     |
| (h) | Miscellaneous                 | Antioxidants, pH Adjusters, Salts, Fragrances, Preservatives, etc. | ≤3 |             | ≤3  | ≤3  | ≤3  |
| (g) |                               | WATER                                                   | qs        | qs          | qs  | qs  | qs  |
|     |                               | pH (+/−0.3)                                             | 4.5       | 4.5         | 4.5 | 4.5 | 4.5 |

In addition to the comparative compositions in the table above (C6-C9), a commercial benchmark product for coloring hair using direct dyes was obtained. The commercial benchmark product, like Inventive Composition D, provides a vivid red color to hair. The ingredients listed on the product are shown below.

| Comparative Commercial Benchmark |
| --- |
| DISILOXANE |
| METHYL TRIMETHICONE |
| TRIETHOXYCAPRYLYLSILANE |
| RED 33 LAKE |
| RED 7 LAKE |
| TRIMETHYLSILOXYSILICATE |
| HYDROFLUOROCARBON 152A |
| BUTANE |

A wash study was carried out to determine the durability (longevity) provided by Inventive Composition D, Comparative Compositions C6-C9, and the Commercial Benchmark. The testing was carried out using 90% grey permed swatches (GP), 90% grey non-permed swatches (NGP), and 25% grey level 8 hair swatches (GL8). Six swatches for each hair type were tested (6 swatches of 90% GP, 6 swatches of GNP, and 6 swatches of GL8; a total of 18 swatches). The hair swatches were treated (colored) with Inventive Composition D, Comparative Compositions C6-C9, The same amount of each composition tested was sprayed onto the hair swatches, massaged into the hair swatches, and the hair swatches allowed to air dry. After about one hour, the swatches were completely dry, and the color was assessed. The results of the color assessment are presented in FIG. 1. The y-axis of the graph reports the ΔE, which is the difference between the initial color value for the hair before coloring and the color value of the swatches after coloring (without washing), based on assessing L*, a*, and b* values.

The color of the hair was assessed using L*, a*, and b* values. The L*a*b* colorimetric system is a colorimetric system that assigns each color to a position in a spherical color space. In this color space, the brightness is represented by a position in the ordinate (z-axis) direction, the hue is represented by a position in the circumferential direction, and the chroma is represented by a distance from the center axis. The position on the ordinate (z-axis) representing brightness is designated by L*, and the L* value changes from 0 corresponding to black to 100 corresponding to white. The positive direction of the x-axis corresponds to a red direction, the positive direction of the y-axis corresponds to a yellow direction, the negative direction of the x-axis corresponds to a green direction, the negative direction of the y-axis corresponds to a blue direction, and the position on the x-axis is designated by a* of which value changes from −60 to +60 and the position on the y-axis is designated by b* of which value changes from −60 to +60. The hue and chroma are represented by a* value and b* value, respectively. The higher the L*, the lighter the color of the hair; the higher the a*, the more the hue shifts to red (i.e., the hair is redder); and the lower the b*, the more the chroma value shifts to blue. Delta-E (ΔE) which is calculated from the L*, a*, and b* values represent the overall color change on the swatches.

After assessing L*a*b* values of the swatches before coloring and after coloring (without washing), the hair swatches were washed with a standard cleansing shampoo (containing 12 wt. % sodium laureth sulfate, pH=5.3+/−0.3) and dried. The washing and drying cycle was carried out twelve times and the color of the swatches assessed. The results after the 12$^{th}$ washing cycle are presented in FIG. 2. The y-axis of the graph reports the ΔE, which is the difference between the initial color value for the hair swatches before coloring and the color value of the swatches after coloring and after being subjected to 12 washing cycles, based on assessing L*, a*, and b* values.

Figure 2:
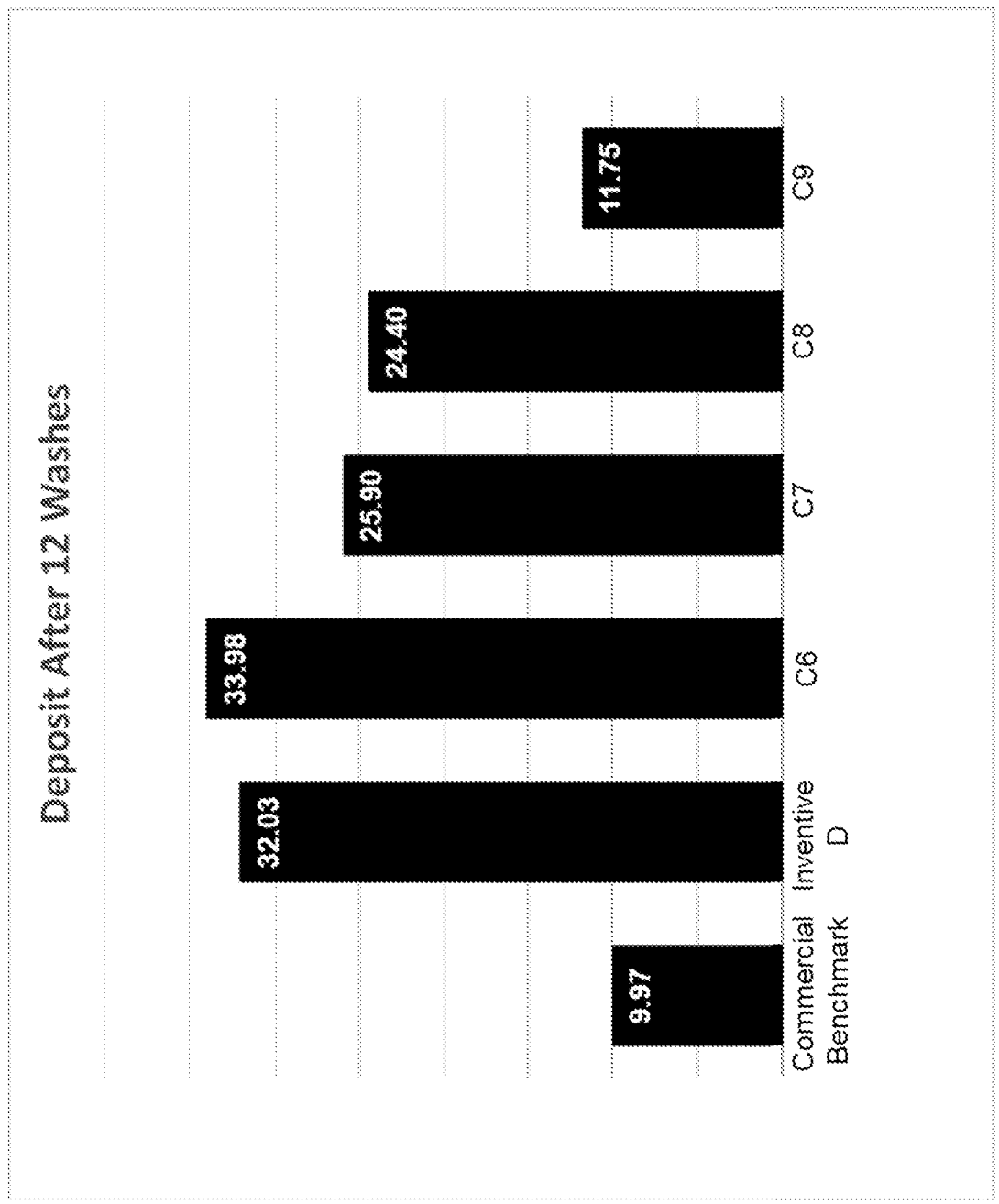
FIG. 2 reports the degree of color change of hair swatches colored with hair coloring compositions according to the instant disclosure and subsequently subjected to twelve wash cycles.

The results in FIG. 2 show that the color from the Commercial Benchmark did not persist—all initial color was largely washed away. The results for the Commercial Benchmark are similar to measurements taken on untreated hair swatches (hair swatches not colored). In fact, the color from the Commercial Benchmark was largely washed away after the first wash (data not shown). After twelve washes, hair treated with Inventive Composition D and Comparative Composition C6 (containing direct dyes in deionized water) retained significantly more color than Comparative Compositions C7-C9. The graph in FIG. 2 shows that Comparative Composition C6 was slightly more colored than Inventive Composition D, but the slight difference is not statistically significant and thus likely represents simple variation. Although Comparative Composition C6 provided durable color lastingness, it lacked the moisturizing and hydrating properties of Inventive Composition D. Hair treated with Comparative Composition C6 was drier and frizzier than hair treated with Inventive Composition D. Furthermore, Inventive Composition D includes PEG-40 hydrogenated castor oil, which functions as a mild cleanser. Despite the inclusion of the mild cleaners, which can negatively impact color deposition, Inventive Composition D imparted long-lasting color deposition on par with Comparative Composition C6, which did not include a mild cleanser.

Inventive Composition D performed significantly better than Comparative Compositions C7-C9 with respect to color tenacity (durability). The results for Comparative Composition C7 illustrate the influence of a polyether-modified polysiloxane (PEG-14 dimethicone) on the formulation. The results for Comparative Composition C8 illustrate the influence of Aloe Baradensis leaf juice on the formulation. The results for Comparative Composition C9 illustrate the influence of a cationic surfactant (hydroxyethyl olely dimonium chloride) on the formulation. If any one of these three elements are omitted from the formulation, the color tenacity (durability) significantly suffers. Furthermore, the Aloe Baradensis leaf juice, the polyether-modified polysiloxane, and the cationic surfactants provide benefits beyond mere color tenacity. The Aloe Baradensis leaf juice has a stabilizing effect on the compositions and provides conditioning properties to the hair. The polyether-modified polysiloxane hydrates the hair and imparts anti-frizz properties. The cationic surfactant (hydroxyethyl olely dimonium chloride) provides conditioning and softening properties to the hair.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

The term "hair" as used herein includes hair of the head, the face (including beard hair and mustache hair), eyebrows, eyelashes, and body hair, unless otherwise specified.

As used herein, the terms "comprising," "having," and "including" are used in their open, non-limiting sense.

A "developer composition" as used herein is a composition containing one or more oxidizing agents, preferably a peroxide (hydrogen peroxide) and is mixed with a hair coloring base composition to form a ready-to-use hair coloring composition.

A "hair coloring base composition" as used herein is a hair coloring composition containing one or more oxidative dye precursors and is mixed with a developer composition to form a ready-to-use hair coloring composition.

A "ready-to-use hair coloring composition" is an "active" composition that includes one or more oxidative dye precursors and one or more oxidizing agents; and is formed by combining a hair coloring base composition with a developer composition.

A "composition colorant" is a compound that colors the composition but does not have an appreciable coloring effect on hair. In other words, the composition colorant is included to provide color to the composition, for example, for aesthetic appeal. It is not included to impart color to the hair. Styling gels, for example, can be found in a variety of different colors (e.g., light blue, light pink, etc.) yet application of the styling gel to the hair does not change the color of the hair.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

Some of the various categories of components identified may overlap. In such cases where overlap may exist and the composition includes both components (or the composition includes more than two components that overlap), an overlapping compound does not represent more than one component. For example, a nonionic surfactant may be considered both a nonionic surfactant and a fatty compound. If a particular composition includes both a nonionic surfactant and a fatty compound, a single compound will serve as only the nonionic surfactant or the fatty compound (the single compound does not serve as both the nonionic surfactant and the fatty component).

The salts referred to throughout the disclosure may include salts having a counter-ion such as an alkali metal, alkaline earth metal, or ammonium counter-ion. This list of counter-ions, however, is non-limiting.

The term "treat" (and its grammatical variations) as used herein refers to the application of the compositions of the present disclosure onto a keratinous substrate such as hair. The term "treat" (and its grammatical variations) as used herein also refers to contacting keratinous substrates such as hair with the compositions of the present disclosure.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

All components positively set forth throughout the instant disclosure may be negatively excluded from the claims, e.g., a claimed composition may be "free," "essentially free" (or "substantially free") of one or more components that are positively set forth in the instant disclosure. As an example, silicones can optionally be included in the compositions but preferably the compositions are free or essentially free from silicones. Silicones are synthetic polymers made up of repeating units of siloxane, elemental silicon and oxygen, combined with other elements, most often carbon and hydrogen. Thus, silicones are also called polysiloxanes.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A hair coloring composition comprising:
    (a) about 1 to about 25 wt. % of aloe barbadensis leaf juice;
    (b) about 1 to about 10 wt. % of one or more polyether-modified polysiloxanes;
    (c) about 0.5 to about 10 wt. % of one or more non-silicone nonionic surfactants selected from alkoxylated compounds;

(d) about 0.05 to about 8 wt. % of one or more cationic surfactants;
(e) optionally, one or more water-soluble organic solvents;
(f) one or more direct dyes; and
(g) water;
wherein the composition is free from oxidative dye precursors, and all weight percentages are based on the total weight of the hair coloring composition.

2. The composition of claim 1, wherein the one or more polyether-modified polysiloxanes are selected from PEG/PPG-18/18 dimethicone, PEG-12 dimethicone, PEG-14 dimethicone, siloxane polyalkyleneoxide copolymer, PEG/PPG-22/24 dimethicone, PEG/PPG-17/18 dimethicone, PEG/PPG-20/6 dimethicone, PEG/PPG-14/4 dimethicone, and mixtures thereof.

3. The composition of claim 1, wherein the one or more non-silicone nonionic surfactants are selected from straight chain primary alcohol alkoxylates, straight chain secondary alcohol alkoxylates, alkyl phenol alkoxylates, olefinic alkoxylates, branched chain alkoxylates, fatty oil or hydrogenated fatty oil ethoxylates, alkyl sorbitan esters ethoxylates, alkyl glyceride ethoxylates, and mixtures thereof.

4. The composition of claim 1, wherein the one or more cationic surfactants are selected from dialkyl dimonium halide compounds.

5. The composition of claim 4, wherein the at least one dialkyl dimonium halide compounds are selected from dicapryl/dicaprylyl dimonium chloride, didecyldimonium chloride, dicetyldimonium chloride, ditallowdimonium chloride, dicocodimonium chloride, distearyldimonium chloride, ceteardimonium chloride, hydroxyethyl oleyl dimonium chloride, panthenyl hydroxypropyl steardimonium chloride, hydroxypropyl bis-hydroxyethyldimonium chloride, hydroxypropyl bisstearyldimonium chloride, hydroxycetyl hydroxyethyl dimonium chloride, hydroxyethyl behenamidopropyl dimonium chloride, behenamidopropyl PG-dimonium chloride, cocamidopropyl PG-dimonium chloride, oleamidopropyl PG-dimonium chloride, and mixtures thereof.

6. The composition of claim 1 comprising the one or more water-soluble organic solvents.

7. The composition of claim 1, wherein the one or more water-soluble organic solvents selected from glycerin, mono-alcohols, polyols (polyhydric alcohols), glycols, and a mixture thereof.

8. The composition of claim 1, wherein the one or more direct dyes are chosen from nitro-phenylenediamines, nitro-aminophenols, azo dyes, anthraquinones, triarylmethane dyes, indophenols, and a combination thereof.

9. The composition of claim 1 in the form of a spray.

10. The composition of claim 1, wherein the composition is essentially free from amino silicones.

11. The composition of claim 1, wherein the composition is essentially free from polyorganosiloxanes other than the polyether-modified polysiloxanes of (c).

12. The composition of claim 1, wherein the composition is free from film forming polymers and/or thickening polymers.

13. The composition of claim 1, further comprising:
(h) about 0.1 to about 10 wt. % of one or more miscellaneous components.

14. The composition of claim 13, wherein the one or more miscellaneous components are selected from antioxidants, pH adjusters, salts, fragrances, preservatives, botanical extracts, chelating agents, vitamins, amino acids, cosmetic colorants, and mixtures thereof.

15. The composition of claim 1 comprising:
(a) about 1 to about 25 wt. % of aloe barbadensis leaf juice;
(b) about 1 to about 10 wt. % of one or more polyether-modified polysiloxanes selected from PEG/PPG-18/18 dimethicone, PEG-12 dimethicone, PEG-14 dimethicone, siloxane polyalkyleneoxide copolymer, PEG/PPG-22/24 dimethicone, PEG/PPG-17/18 dimethicone, PEG/PPG-20/6 dimethicone, PEG/PPG-14/4 dimethicone, and mixtures thereof;
(c) about 0.5 to about 10 wt. % of one or more non-silicone nonionic surfactants selected from straight chain primary alcohol alkoxylates, straight chain secondary alcohol alkoxylates, alkyl phenol alkoxylates, olefinic alkoxylates, branched chain alkoxylates, fatty oil or hydrogenated fatty oil ethoxylates, alkyl sorbitan esters ethoxylates, alkyl glyceride ethoxylates, and mixtures thereof;
(d) about 0.05 to about 8 wt. % of one or more cationic surfactants selected from dialkyl dimonium halide compounds;
(e) about 0.05 to about 15 wt. % of one or more water-soluble organic solvents selected from glycerin, mono-alcohols, polyols (polyhydric alcohols), glycols, and a mixture thereof;
(f) one or more direct dyes; and
(g) about 60 to about 92 wt. % of water; and
(h) about 0.1 to about 10 wt. % of one or more miscellaneous components selected from antioxidants, pH adjusters, salts, fragrances, preservatives, botanical extracts, chelating agents, vitamins, amino acids, cosmetic colorants, and mixtures thereof;
wherein the composition is free from oxidative dye precursors, and all weight percentages are based on the total weight of the hair coloring composition.

16. The composition of claim 15 comprising:
(a) about 1 to about 25 wt. % of aloe barbadensis leaf juice;
(b) about 1 to about 10 wt. % of one or more polyether-modified polysiloxanes selected from PEG/PPG-18/18 dimethicone, PEG-12 dimethicone, PEG-14 dimethicone, siloxane polyalkyleneoxide copolymer, PEG/PPG-22/24 dimethicone, PEG/PPG-17/18 dimethicone, PEG/PPG-20/6 dimethicone, PEG/PPG-14/4 dimethicone, and mixtures thereof;
(c) about 0.5 to about 10 wt. % of one or more non-silicone nonionic surfactants selected from fatty oil and hydrogenated fatty oil ethoxylates;
(d) about 0.05 to about 8 wt. % cationic surfactants selected from dialkyl dimonium halide compounds;
(e) about 0.05 to about 15 wt. % of one or more water-soluble organic solvents selected from glycerin, mono-alcohols, polyols (polyhydric alcohols), glycols, and a mixture thereof;
(f) one or more cationic direct dyes; and
(g) about 60 to about 92 wt. % of water; and
(h) about 0.1 to about 10 wt. % of one or more miscellaneous components selected from antioxidants, pH adjusters, salts, fragrances, preservatives, botanical extracts, chelating agents, vitamins, amino acids, cosmetic colorants, and mixtures thereof;
wherein all weight percentages are based on the total weight of the hair coloring composition.

17. A method for coloring hair comprising applying the hair coloring composition of claim 1 to the hair.

18. The method of claim 17, wherein the hair coloring composition is applied the hair by spraying the hair coloring composition onto the hair.

19. The method of claim 17, wherein the hair coloring composition is applied to dry hair.

* * * * *